(12) United States Patent
Schulman et al.

(10) Patent No.: US 7,235,050 B2
(45) Date of Patent: Jun. 26, 2007

(54) IMPLANTABLE DEVICE FOR PROCESSING NEUROLOGICAL SIGNALS

(75) Inventors: Joseph H. Schulman, Santa Clarita, CA (US); Christian Perron, Quebec (CA)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 379 days.

(21) Appl. No.: 10/920,544

(22) Filed: Aug. 18, 2004

(65) Prior Publication Data

US 2005/0085864 A1  Apr. 21, 2005

Related U.S. Application Data

(63) Continuation-in-part of application No. 10/121,881, filed on Apr. 11, 2002, now Pat. No. 6,990,372.

(60) Provisional application No. 60/497,383, filed on Aug. 22, 2003.

(51) Int. Cl.
*A61B 5/04* (2006.01)

(52) U.S. Cl. .................. 600/300; 600/509; 600/544; 600/546; 607/2; 607/62; 128/902

(58) Field of Classification Search ............... 600/300, 600/301, 509, 544, 546; 607/1, 2, 17, 36, 607/39–41, 45, 46, 50, 60, 62; 128/902
See application file for complete search history.

(56) References Cited

U.S. PATENT DOCUMENTS

| | | | | |
|---|---|---|---|---|
| 3,579,138 A | * | 5/1971 | Harris et al. ................. 330/86 |
| 3,628,538 A | * | 12/1971 | Vincent et al. ............... 607/62 |
| 3,641,993 A | * | 2/1972 | Gaarder et al. ............. 600/546 |
| 4,964,411 A | * | 10/1990 | Johnson et al. ............. 600/546 |
| 5,012,199 A | * | 4/1991 | McKale ........................ 330/51 |
| 5,117,824 A | * | 6/1992 | Keimel et al. ................. 607/4 |
| 5,358,514 A | * | 10/1994 | Schulman et al. ............ 607/61 |
| 5,957,857 A | * | 9/1999 | Hartley ........................ 600/521 |
| 6,118,989 A | * | 9/2000 | Abe et al. ................. 455/127.2 |
| 6,164,284 A | | 12/2000 | Schulman et al. |
| 6,185,452 B1 | | 2/2001 | Schulman et al. |
| 6,208,894 B1 | | 3/2001 | Schulman et al. |
| 6,315,721 B2 | | 11/2001 | Schulman et al. |
| 6,564,807 B1 | | 5/2003 | Schulman et al. |
| 6,750,713 B1 | * | 6/2004 | Wyszynski .................. 330/254 |
| 2001/0001125 A1 | | 5/2001 | Schulman et al. |

FOREIGN PATENT DOCUMENTS

WO   WO 03 086184 A1   10/2003

* cited by examiner

*Primary Examiner*—Kennedy Schaetzle
(74) *Attorney, Agent, or Firm*—Malcolm J. Romano

(57) ABSTRACT

An implantable device comprising a sensing unit, wherein the sensing unit is adapted to rectify biological/neurological signals in the form of sensed electrical signals from body tissue adjacent to the location of the implantable device. The sensing unit of the implantable device comprises at least one amplifier, wherein the supply current to the at least one amplifier is responsive to the magnitude of the sensed electrical signals provided to the at least one amplifier. The implantable device is further capable of integrating the rectified sensed electrical signals and generating output signals, wherein the output signals contain indicia of biopotential parameters of the body tissue.

20 Claims, 17 Drawing Sheets

OPEN LOOP CONTROL/MONITOR

CLOSED LOOP CONTROL

EXEMPLARY INJURY

COORDINATED CLOSED LOOP HAND CONTROL

IMPLANTABLE DEVICE FOR PROCESSING NEUROLOGICAL SIGNALS

This application is a continuation-in-part of U.S. patent application Ser. No. 10/121,881, filed Apr. 11, 2002, which issued as U.S. Pat. No. 6,990,372 on Jan. 24, 2006. This application also claims the benefit of U.S. Provisional Application Ser. No. 60/497,383, filed on Aug. 22, 2003. The subject matter of all of the aforementioned applications are hereby incorporated by reference herein in their entirety.

DETAILED DESCRIPTION OF THE PREFERRED EMBODIMENTS

Figure 1:
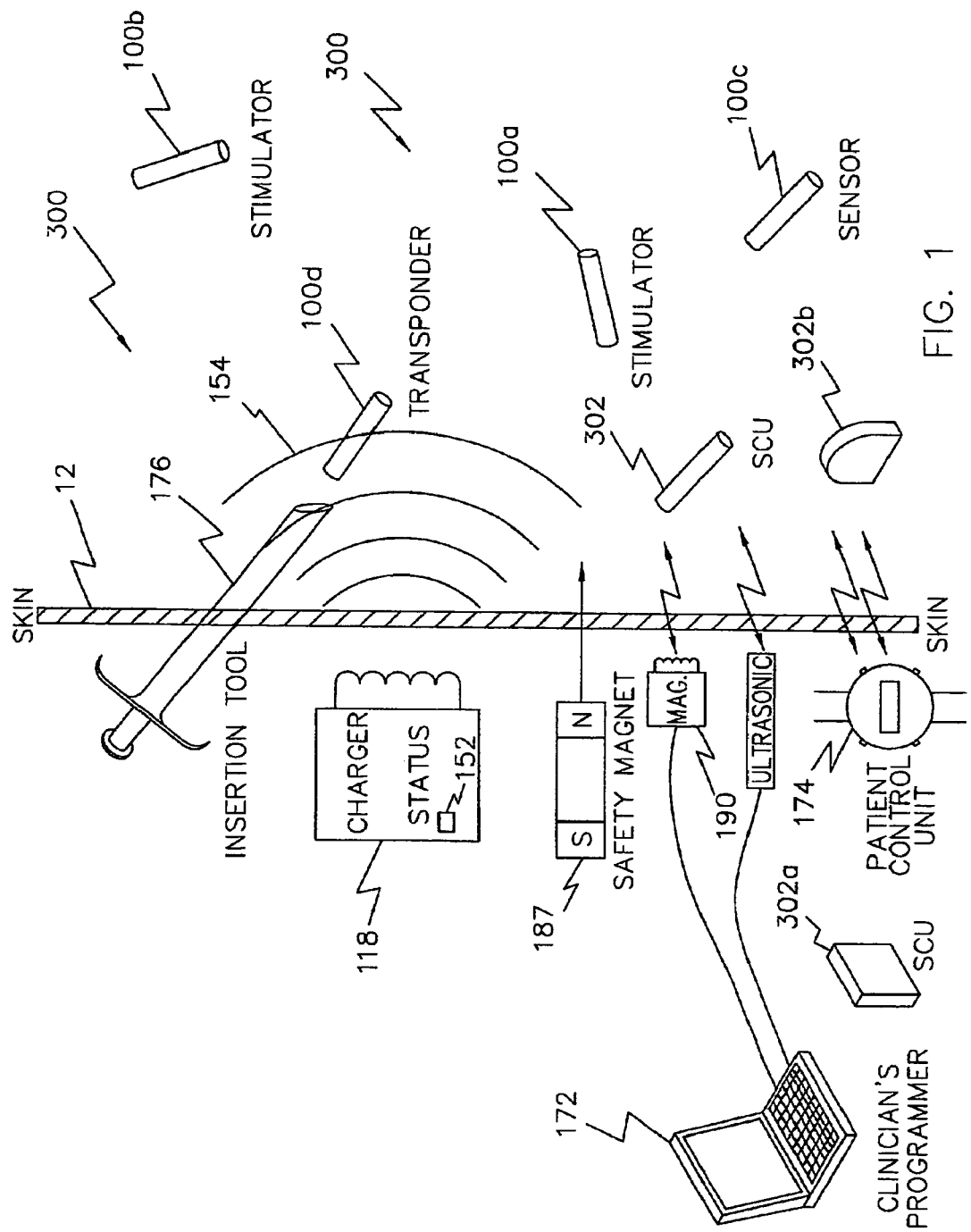
FIG. 1 is a simplified block diagram of an exemplary system suitable for practicing the present invention, the system being comprised of implanted devices, e.g., microstimulators, microsensors and microtransponders, under control of an implanted system control unit (SCU).

The following description is of the best mode presently contemplated for carrying out the invention. This description is not to be taken in a limiting sense, but is made merely for the purpose of describing the general principles of the invention. The scope of the invention should be determined with reference to the claims.

The present invention relates to devices and systems of such devices for monitoring and/or affecting parameters of a patient's body for the purpose of medical diagnosis and/or treatment. More particularly, such devices, preferably battery powered, are configured for implanting within a patient's body, each device being configured to sense a body parameter, e.g., temperature, O2 content, physical position, electrical potential, etc., and/or to affect a parameter, e.g., via nerve and/or muscle stimulation.

Commonly owned U.S. Pat. Nos. 6,164,284; 6,208,894; 6,315,721; and 6,564,807 each entitled "System of Implantable Devices For Monitoring and/or Affecting Body Parameters" and U.S. Pat. No. 6,185,452 entitled "Battery Powered Patient Implantable Device", each incorporated herein by reference in their entirety, describe devices configured for implantation within a patient's body, i.e., beneath a patient's skin, for performing various functions including: (1) stimulation of body tissue and/or sensing of body parameters, and (2) communicating between implanted devices and devices external to a patient's body. In an exemplary use, the implanted device is used to electrically stimulate a neural pathway and/or muscle and the same (and/or another) implanted device senses an evoked response from the intended muscle tissue and uses the detected signal to confirm that stimulation did occur and/or to achieve closed loop control. In general, the detected signal may exhibit a frequency component that corresponds to the intensity of the intended or actual muscle response and amplitude components that correspond to its proximity to the desired source tissue and/or other signal generating tissue. Depending on the application, there are various techniques that may be used to interpret the neurological signal. Such implantable devices are preferably powered using rechargeable batteries and it is desired that the time between rechargings be maximized by minimizing the power dissipation of such circuitry within these implantable devices. Accordingly, what is needed is a programmable signal analysis circuit that can be configured to interpret neurological signals using a plurality of analysis modes. Furthermore, such a circuit should minimize its power dissipation to thus enhance the battery life of the implantable devices.

A preferred signal analysis device for use within an implantable device, wherein the implantable device is configured at least in part for sensing a biological signal within a patient's body and the implantable device is contained within a sealed elongate housing having an axial dimension of less than 60 mm and a lateral dimension of less than 6 mm, comprises: (1) sensing circuitry for receiving a biological signal within the implantable device and generating a sensed voltage output in response thereto; (2) event detection circuitry for detecting an attribute of the sensed output according to one or more designated criteria and designating the detected attribute as an event; (3) an event counter configured for accumulating detected events; (4) a clocked counter for accumulating clock pulses; and (5) event analysis circuitry for determining a processed value corresponding to the detected events and the accumulated clock pulses.

In a further aspect of a preferred embodiment of the present invention, the event analysis circuitry is configurable to operate in a plurality of modes, e.g., a mode which determines the rate at which detected events occur, a mode which determines the number of events that occur within a designated time period, a mode which determines the amount of time between a start time and the first detected event, etc.

In a still further aspect of a preferred embodiment of the present invention, the event detection circuitry determines whether an event occurred according to one or according to two or more programmable criteria, e.g., amplitude threshold levels. Alternatively or additionally, a peak detector may be used to determine events. Additionally, the event detection circuitry may be comprised in part of two digital to analog converters that convert programmable digital threshold values into analog threshold values that are compared with a sensed analog neurological signal value to determine when the neurological signal is above or below the programmed threshold values. These comparisons are then programmably used to identify (or to exclude) events.

The novel features of the invention are set forth with particularity in the appended claims. The invention will be best understood from the following description when read in conjunction with the accompanying drawings.

The present invention is generally directed to circuitry for use within implantable medical devices and in particular to such circuits which sense neurological signals, e.g., from nerves or muscles, to detect intended or actual muscle stimulation. In an exemplary embodiment for the present invention, such circuits may be used within implanted devices configured similarly to the devices described in the commonly owned U.S. Pat. No. 6,164,284. Such implanted devices typically comprise a sealed housing suitable for injection into the patient's body and preferably contain a power source, e.g., a battery, having a capacity of at least 1 microwatt-hour and power consuming circuitry preferably including a data signal transmitter and receiver and sensor/stimulator circuitry for driving an input/output transducer. In a typical application, such devices are used to stimulate a neural pathway or muscle and/or to block a neural pathway to alleviate pain or block stimulation of a muscle. The present invention is thus specifically directed to an implementation of the sensor circuitry for use in such an implantable device.

In an exemplary system of devices which use the signal analysis device of the present invention, a system control unit (SCU) comprises a programmable unit capable of (1) transmitting commands to at least some of a plurality of implantable devices and (2) receiving data signals from at least some of those implantable devices. Such a system preferably operates, at least in part, in closed loop fashion whereby the commands transmitted by the SCU are dependent, in part, on the content of the data signals received by the SCU.

Figure 2:
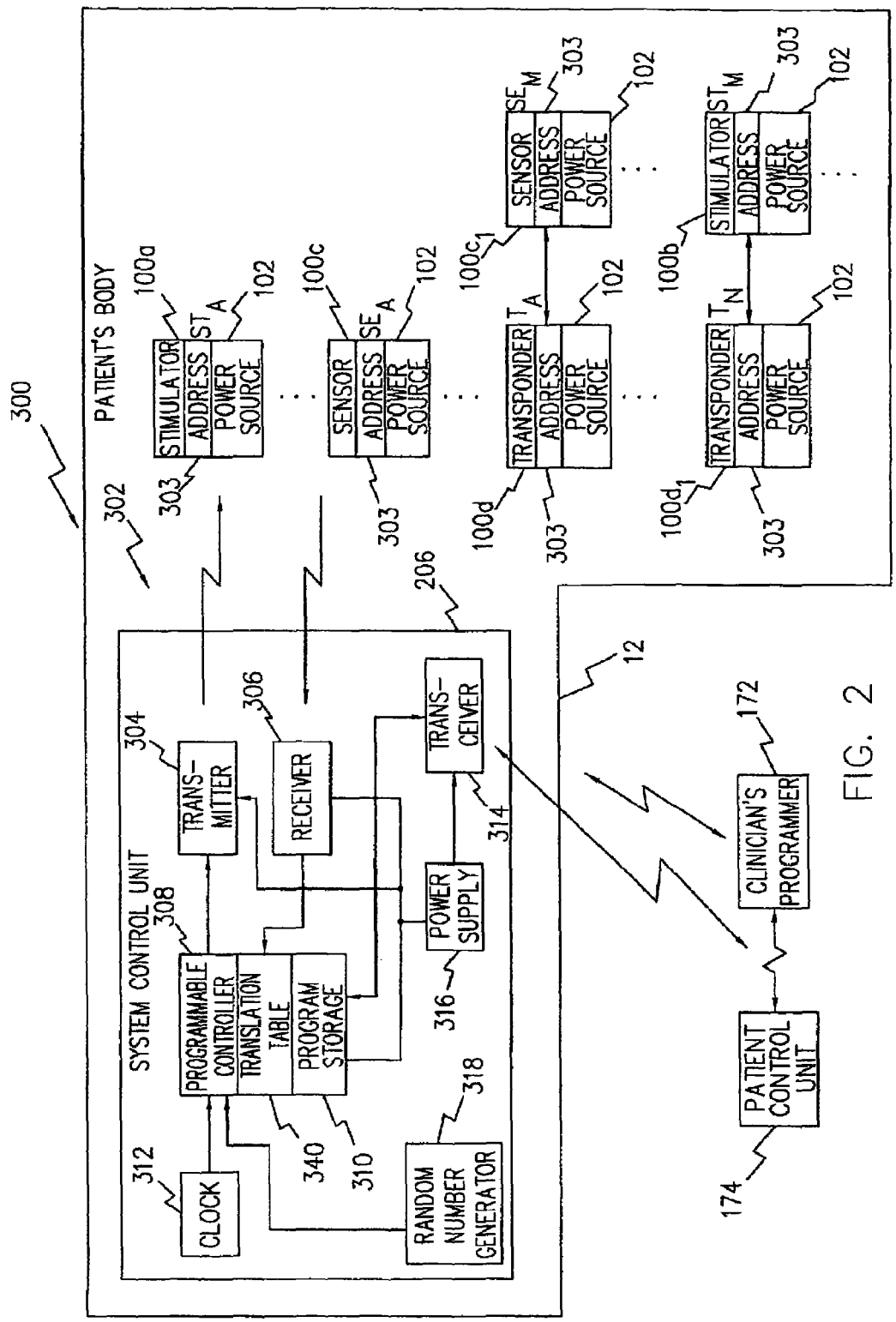
FIG. 2 comprises a block diagram of the system of FIG. 1 showing the functional elements that form the system control unit and implanted microstimulators, microsensors and microtransponders.

FIGS. 1 and 2 show an exemplary system 300 made of implanted devices 100, preferably battery powered, under control of a system control unit (SCU) 302, preferably also implanted beneath a patient's skin 12. As described in the '284 patent, potential implanted devices 100 (see also the block diagram shown in FIG. 3A) include stimulators, e.g., 100a and 100b, sensors, e.g., 100c, and transponders, e.g., 100d. The stimulators, e.g., 100a, can be remotely programmed to output a sequence of drive pulses to body tissue proximate to its implanted location via attached electrodes. The sensors, e.g., 100c, can be remotely programmed to sense one or more physiological or biological parameters in the implanted environment of the device, e.g., temperature, glucose level, O2 content, nerve potential, muscle potential, etc. Transponders, e.g., 100d, are devices which can be used to extend the interbody communication range between stimulators and sensors and other devices, e.g., a clinician's programmer 172 and the patient control unit 174. Preferably, these stimulators, sensors and transponders are contained in sealed elongate housings having an axial dimension of less than 60 mm and a lateral dimension of less than 6 mm. Accordingly, such stimulators, sensors and transponders are respectively referred to as microstimulators, microsensors, and microtransponders or referred to in general as battery-powered, implantable stimulator/sensor devices. Such microstimulators and microsensors can thus be positioned beneath the skin 12 within a patient's body using a hypodermic type insertion tool 176.

As described in the '284 patent, microstimulators and microsensors are remotely programmed and interrogated via a wireless communication channel, e.g., modulated AC magnetic, sound (i.e., ultrasonic), RF or electric fields, typically originating from control devices external to the patient's body, e.g., the clinician's programmer 172 or patient control unit 174. Typically, the clinician's programmer 172 is used to program a single continuous or one time pulse sequence into each microstimulator and/or measure a biological parameter from one or more microsensors. Similarly, the patient control unit 174 typically communicates with the implanted devices 100, e.g., microsensors 100c, to monitor biological parameters. In order to distinguish each implanted device over the communication channel, each implanted device is manufactured with an address or identification code (ID) 303 specified in address storage circuitry 108 (see FIG. 3A) as described in the '284 patent.

By using one or more such implantable devices in conjunction with the SCU 302 of the present invention, the capabilities of such implanted devices can be further expanded. For example, in an open loop mode (described below in reference to FIG. 4), the SCU 302 can be programmed to periodically initiate tasks, e.g., perform real time tasking, such as transmitting commands to microstimulators according to a prescribed treatment regimen or periodically monitor biological parameters to determine a patient's status or the effectiveness of a treatment regimen. Alternatively, in a closed loop mode (described below in reference to FIGS. 5-7), the SCU 302 periodically interrogates one or more microsensors and accordingly adjusts the commands transmitted to one or more microstimulators.

FIG. 2 shows a system 300 comprised of (1) one or more implantable devices 100 operable to sense and/or stimulate a patient's body parameter in accordance with one or more controllable operating parameters and (2) the SCU 302. The SCU 302 is primarily comprised of (1) a housing 206, preferably sealed and configured for implantation beneath the skin of the patient's body as described in the '284 patent in reference to the implanted devices 100, (2) a signal transmitter 304 in the housing 206 for transmitting command signals, (3) a signal receiver 306 in the housing 206 for receiving status signals, and (4) a programmable controller 308, e.g., a microcontroller or state machine, in the housing 206 responsive to received status signals for producing command signals for transmission by the signal transmitter 304 to other implantable devices 100. The sequence of operations of the programmable controller 308 is determined by an instruction list, i.e., a program, stored in program storage 310, coupled to the programmable controller 308. While the program storage 310 can be a nonvolatile memory device, e.g., ROM, manufactured with a program corresponding to a prescribed treatment regimen, it is preferable that at least a portion of the program storage 310 be an alterable form of memory, e.g., RAM, EEPROM, etc., whose contents can be remotely altered as described further below. However, it is additionally preferable that a portion of the program storage 310 be nonvolatile so that a default program is always present. The rate at which the program contained within the program storage 310 is executed is determined by clock/oscillator 312. Additionally, a real time clock operating in response to clock/oscillator 312 preferably permits tasks to be scheduled at specified times of day.

The signal transmitter 304 and signal receiver 306 preferably communicate with implanted devices 100 using an RF signal, e.g., a propagated electromagnetic wave, modulated by a command data signal. Alternatively, an audio transducer may be used to generate mechanical vibrations having a carrier frequency modulated by a command data signal. In an exemplary system, a carrier frequency of 100 kHz is used which corresponds to a frequency that freely passes through a typical body's fluids and tissues. However, such sound means that operate at any frequency, e.g., greater than 1 Hz, are also considered to be usable with such devices. Alternatively, the signal transmitter 304 and signal receiver 306 can communicate using modulated AC, e.g., magnetic fields.

The clinician's programmer 172 and/or the patient control unit 174 and/or other external control devices can also communicate with the implanted devices 100, as described in the '284 patent, preferably using a modulated RF or AC magnetic field. Alternatively, such external devices can communicate with the SCU 302 via a transceiver 314 coupled to the programmable controller 308. Since, the signal transmitter 304 and signal receiver 306 may operate using a different communication means, a separate transceiver 314 which operates using an alternative communication means may be used for communicating with external devices. However, a single transmitter 304/receiver 306 can be used in place of transceiver 314 for communicating with the external devices and implanted devices if a common communication means is used.

Figure 3A:
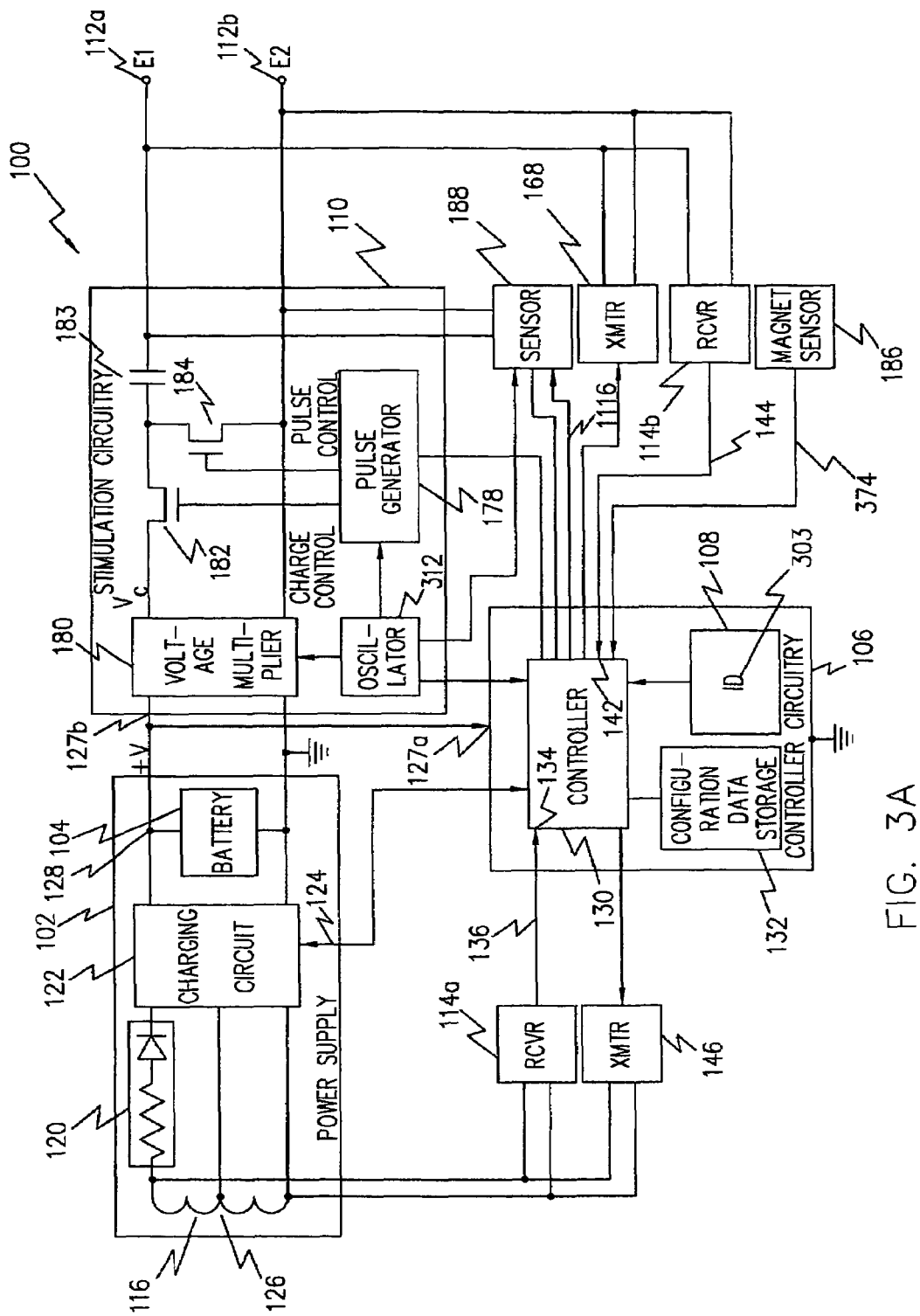
FIG. 3A comprises a block diagram of an exemplary implantable device, as shown in U.S. Pat. No. 6,164,284, including a battery for powering the device for a period of time in excess of one hour in response to a command from the system control unit.
Figure 3B:
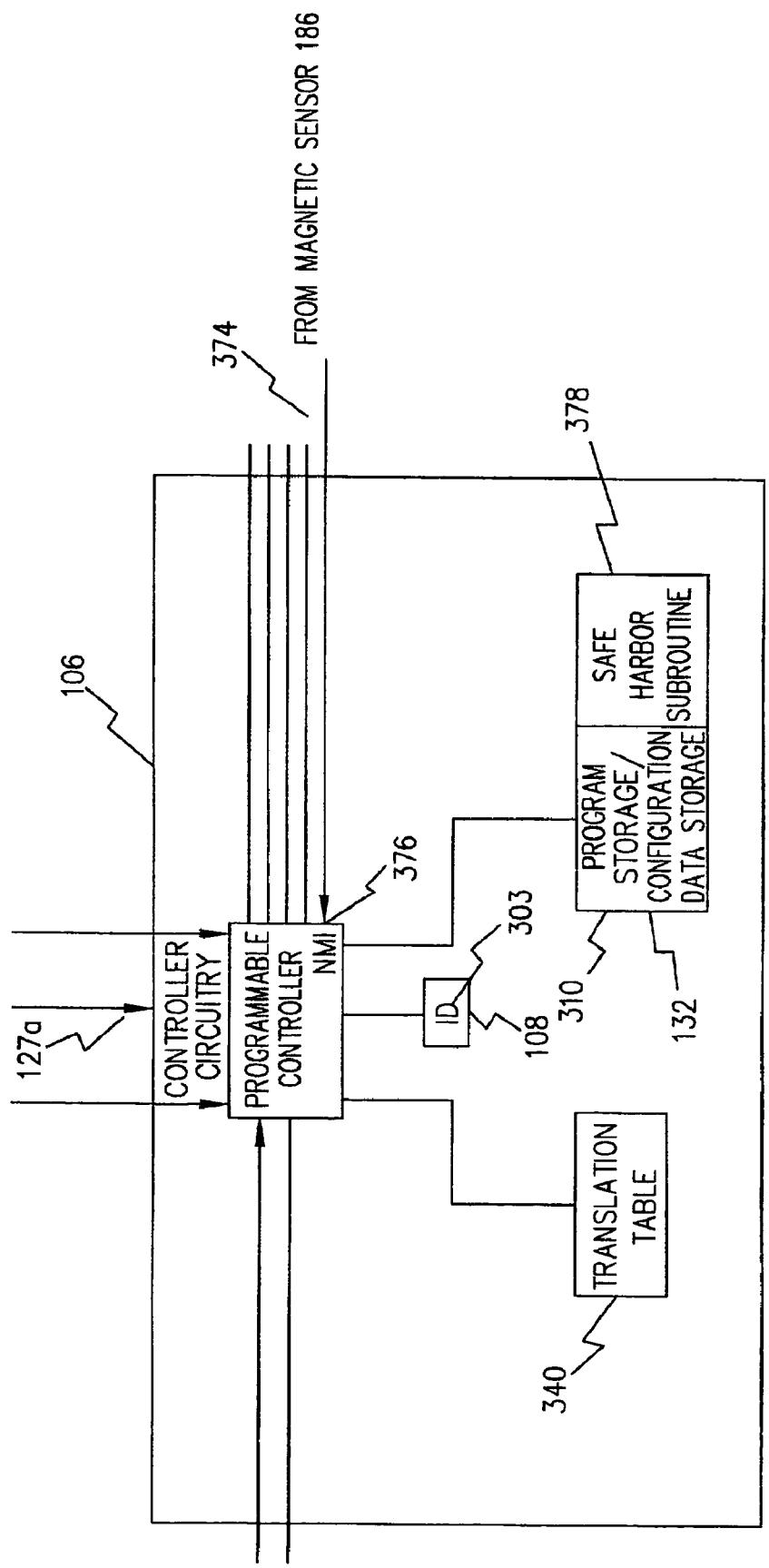
FIG. 3B comprises a simplified block diagram of controller circuitry that can be substituted for the controller circuitry of FIG. 3A, thus permitting a single device to be configured as a system control unit and/or a microstimulator and/or a microsensor and/or a microtransponder.

FIG. 3A comprises a block diagram of an exemplary implantable device 100 operable under control of controller circuitry 106 and includes a battery 104, preferably rechargeable, for powering the device for a period of time in excess of one hour and responsive to command signals from a remote device, e.g., the SCU 302. The controller circuitry 106 is primarily comprised of a controller 130, configuration data storage 132 for prescribing its operation, and address storage circuitry 108 for storing the ID 303 of the device. As described in the '284 patent, the implantable device 100 is preferably configurable to alternatively operate as a microstimulator and/or microsensor and/or microtransponder due to the commonality of most of the circuitry contained within. Such circuitry may be further expanded to permit a common block of circuitry to also perform the functions required for the SCU 302. Accordingly, FIG. 3B shows an alternative implementation of the controller circuitry 106 of FIG. 3A that is suitable for implementing a microstimulator and/or a microsensor and/or a microtransponder and/or the SCU 302. In this implementation, the configuration data storage 132 can be alternatively used as the program storage 310 when the implantable device 100 is used as the SCU 302. In this implementation, XMTR 168 corresponds to the signal transmitter 304 and the RCVR 114b corresponds to the signal receiver 306 (preferably operable via electrodes 112a and 112b operating as an RF antenna) and the RCVR 114a and XMTR 146 correspond to the transceiver 314 (preferably operable via coil 116 for AC magnetic modes of communication).

In a preferred design, the contents of the program storage 310, i.e., the software that controls the operation of the programmable controller 308, can be remotely downloaded, e.g., from the clinician's programmer 172 using data modulated onto an RF signal or an AC magnetic field. In this design, it is preferable that the contents of the program storage 310 for each SCU 302 be protected from an inadvertent change. Accordingly, the contents of the address storage circuitry 108, i.e., the ID 303, is preferably used as a security code to confirm that the new program storage contents are destined for the SCU 302 receiving the data. This feature is significant if multiple patient's could be physically located, e.g., in adjoining beds, within the communication range of the clinician's programmer 172.

In a further aspect of the present invention, it is preferable that the SCU 302 be operable for an extended period of time, e.g., in excess of one hour, from an internal power supply 316 (see FIG. 2). While a primary battery, i.e., a nonrechargeable battery, is suitable for this function, it is preferable that the power supply 316 include a rechargeable battery, e.g., battery 104 as described in the '284 patent, that can be recharged via an AC magnetic field produced external to the patient's body. Accordingly, power supply 102 of FIG. 3A is the preferred power supply 316 for the SCU 302 as well.

The battery-powered devices 100 of the '284 patent are preferably configurable to operate in a plurality of operational modes, e.g., via a communicated command signal. In a first operational mode, device 100 is remotely configured to be a microstimulator, e.g., 100a and 100b. In this design (see FIG. 3A), controller 130 commands stimulation circuitry 110 to generate a sequence of drive pulses through electrodes 112 to stimulate tissue, e.g., a nerve or muscle, proximate to the implanted location of the microstimulator, e.g., 100a or 100b. In operation, a programmable pulse generator 178 and voltage multiplier 180 are configured with parameters (see exemplary Table I) corresponding to a desired pulse sequence and specifying how much to multiply (or divide) the battery voltage (e.g., by summing charged capacitors or similarly charged battery portions) to generate a desired compliance voltage Vc. A first FET 182 is periodically energized to store charge into capacitor 183 (in a first direction at a low current flow rate through the body tissue) and a second FET 184 is periodically energized to discharge capacitor 183 in an opposing direction at a higher current flow rate which stimulates a nearby muscle or nerve. Alternatively, electrodes can be selected that will form an equivalent capacitor within the body tissue.

TABLE I

Stimulation Parameters

| | |
|---|---|
| Current: | continuous current charging of storage capacitor |
| Charging currents: | 1, 3, 10, 30, 100, 250, 500 µA |
| Current Range: | 0.8 to 40 mA in nominally 3.2% steps |
| Compliance Voltage: | selectable, 3-24 volts in 3 volt steps |
| Pulse Frequency (PPS): | 1 to 5000 PPS in nominally 30% steps |
| Pulse Width: | 5 to 2000 µs in nominally 10% steps |
| Burst On Time (BON): | 1 ms to 24 hours in nominally 20% steps |
| Burst Off Time (BOF): | 1 ms to 24 hours in nominally 20% steps |

TABLE I-continued

Stimulation Parameters

| | |
|---|---|
| Triggered Delay to BON: | either selected BOF or pulse width |
| Burst Repeat Interval: | 1 ms to 24 hours in nominally 20% steps |
| Ramp On Time: | 0.1 to 100 seconds (1, 2, 5, 10 steps) |
| Ramp Off Time: | 0.1 to 100 seconds (1, 2, 5, 10 steps) |

In a next operational mode, the battery-powered implantable device 100 can be configured to operate as a microsensor, e.g., 100c, that can sense one or more physiological or biological parameters in the implanted environment of the device. In accordance with a preferred mode of operation, the system control unit 302 periodically requests the sensed data from each microsensor 100c using its ID 303 stored in the address storage circuitry 108, and responsively sends command signals to microstimulators, e.g., 100a and 100b, adjusted accordingly to the sensed data. For example, sensor circuitry 188 can be coupled to the electrodes 112 to sense or otherwise used to measure a biological parameter, e.g., temperature, glucose level, O2 content, voltage, current, impedance, etc., and provide the sensed data to the controller circuitry 106. Preferably, the sensor circuitry 188 includes a programmable bandpass filter and an analog to digital (A/D) converter that can sense and accordingly convert the voltage levels across the electrodes 112 into a digital quantity. Alternatively, the sensor circuitry 188 may include one or more comparators for determining if the measured voltage exceeds a threshold voltage value or is within a specified voltage range, i.e., an amplitude window, and/or peak detectors for determining peaks of the sensed signals, i.e., zero slope points. Each of these attributes, i.e., qualified amplitudes or slopes, may be determined to be events. Furthermore, the sensor circuitry 188 of the present invention additionally includes counters, i.e., accumulators, which track the occurrences of these events to determine event rates, evoked response times, or the like and/or to determine if events occur within specified time periods, i.e., time windows. The sensor circuitry of the present invention will be discussed in detail further below.

The operational mode of the front end processing, e.g., the bandpass filter portion of the sensor circuitry 188 is remotely programmable via the device's communication interface (see exemplary Table II).

TABLE II

Sensing Parameters

| | |
|---|---|
| Input voltage range: | 5 μV to 1 V |
| Bandpass filter rolloff: | 24 dB |
| Low frequency cutoff choices: | 10, 30, 100, 300, 1000, 3000 Hz |
| High frequency cutoff choices: | 300, 1000, 3000, 10000 Hz |
| Integrator frequency choices: | 1 PPS to 100 PPS |
| Amplitude threshold for detection choices: | 4 bits of resolution |

Additionally, the sensing capabilities of a microsensor may include the capability to monitor the battery status via path 124 from the charging circuit 122 and can additionally include using an ultrasonic transducer (not shown) or the coil 116 to respectively measure the ultrasonic, magnetic or propagated RF signal magnitudes (or communication time delays) of signals transmitted between a pair of implanted devices and thus determine the relative locations of these devices. This information can be used to determine the amount of body movement, e.g., the amount that an elbow or finger is bent, and thus form a portion of a closed loop motion control system.

Figure 4:
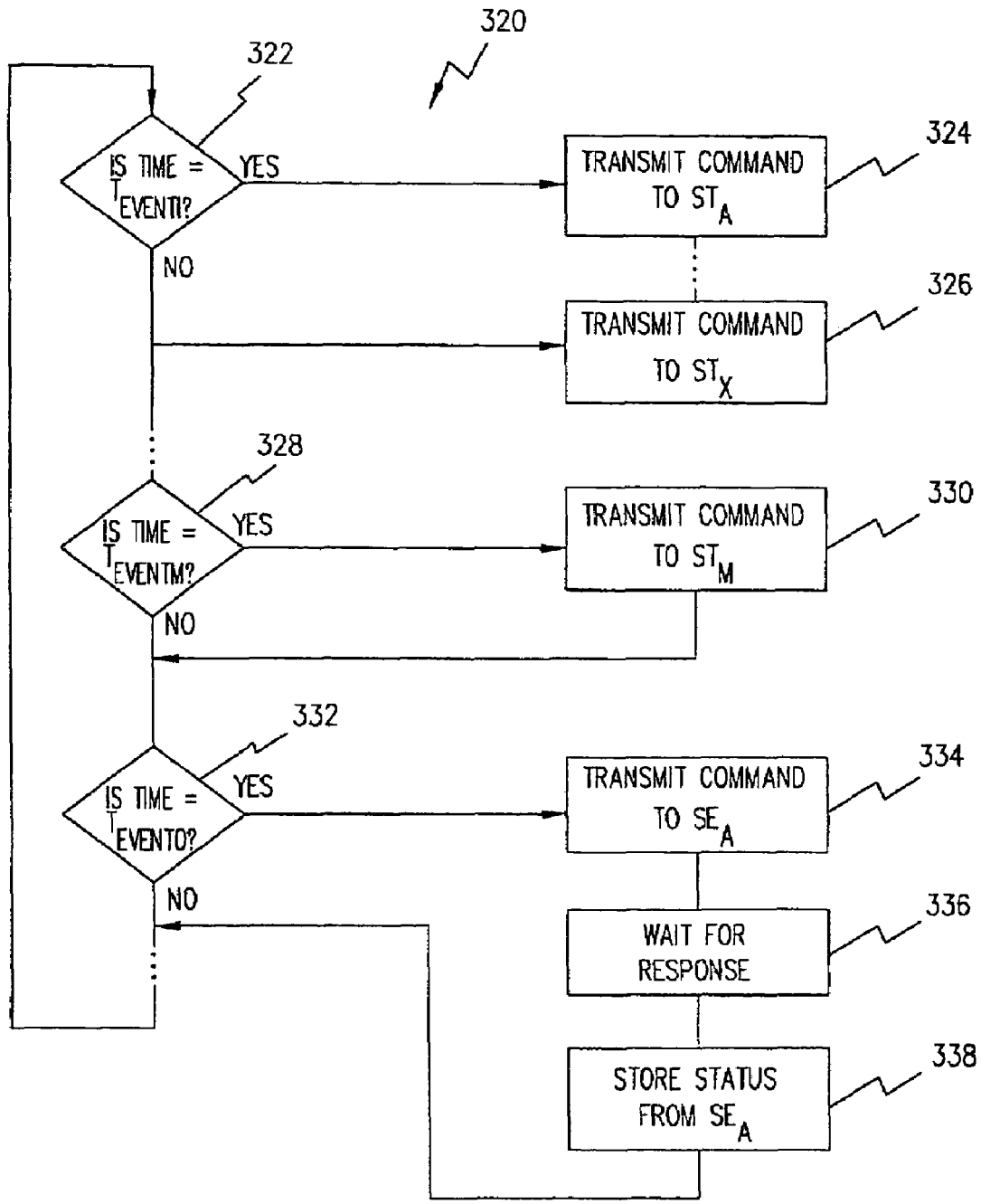
FIG. 4 shows an exemplary flow chart of the use of the exemplary system in an open loop mode for controlling/monitoring a plurality of implanted devices, e.g., microstimulators, microsensors.

FIG. 4 shows a block diagram of an exemplary open loop control program, i.e., a task scheduler 320, for controlling/monitoring a body function/parameter. In this process, the programmable controller 308 is responsive to the clock 312 (preferably a crystal controlled oscillator to thus permit real time scheduling) in determining when to perform any of a plurality of tasks. In this exemplary flow chart, the programmable controller 308 first determines in block 322 if it is now at a time designated as TEVENT1 (or at least within a sampling error of that time), e.g., at 1:00 AM. If so, the programmable controller 308 transmits a designated command to microstimulator A (STA) in block 324. In this example, the control program continues where commands are sent to a plurality of stimulators and concludes in block 326 where a designated command is sent to microstimulator X (STX). Such a subprocess, e.g., a subroutine, is typically used when multiple portions of body tissue require stimulation, e.g., stimulating a plurality of muscle groups in a paralyzed limb to avoid atrophy. The task scheduler 320 continues through multiple time event detection blocks until in block 328 it determines whether the time TEVENTM has arrived. If so, the process continues at block 330 where, in this case, a single command is sent to microstimulator M (STM). Similarly, in block 332 the task scheduler 320 determines when it is the scheduled time, i.e., TEVENTO, to execute a status request from microsensor A (SEA). If so, a subprocess, e.g., a subroutine, commences at block 334 where a command is sent to microsensor A (SEA) to request sensor data and/or specify sensing criteria. Microsensor A (SEA) does not instantaneously respond. Accordingly, the programmable controller 308 waits for a response in block 336. In block 338, the returned sensor status data from microsensor A (SEA) is stored in a portion of the memory, e.g., a volatile portion of the program storage 310, of the programmable controller 308. The task scheduler 320 can be a programmed sequence, i.e., defined in software stored in the program storage 310, or, alternatively, a predefined function controlled by a table of parameters similarly stored in the program storage 310. A similar process may be used where the SCU 302 periodically interrogates each implantable device 100 to determine its battery status.

Figure 5:
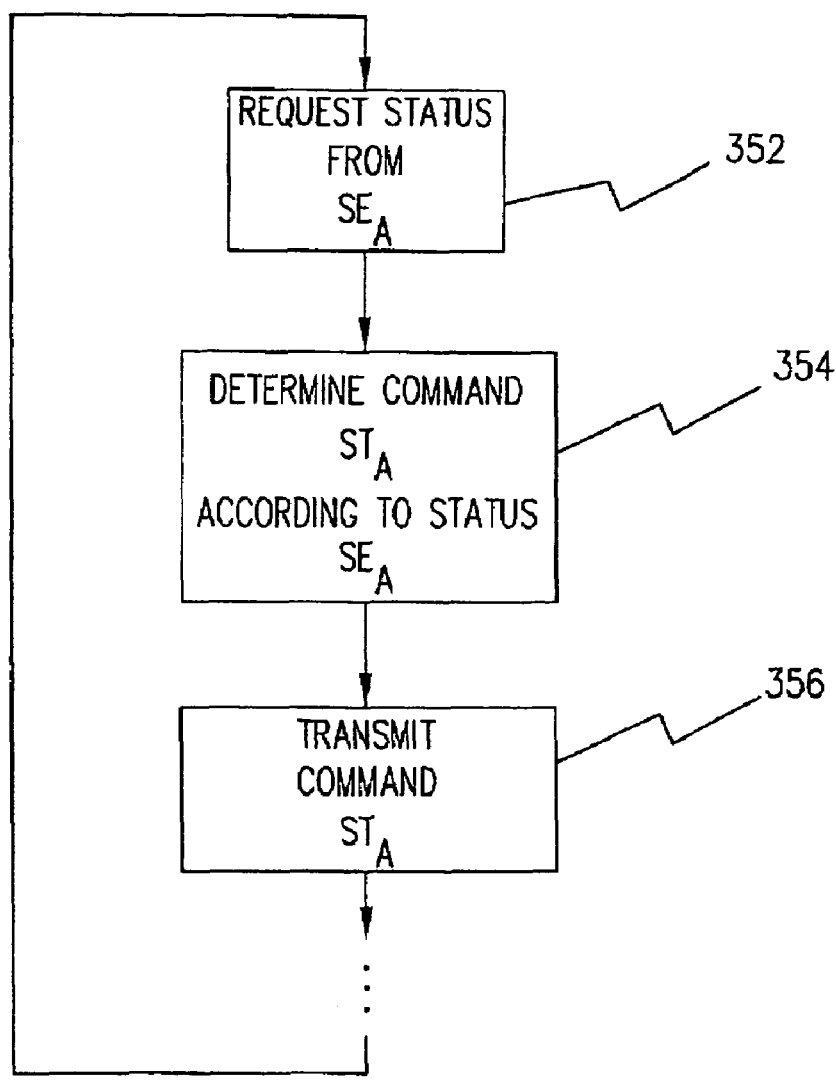
FIG. 5 shows a simplified flow chart of the use of closed loop control of a microstimulator by altering commands from the system control unit in response to status data received from a microsensor.

FIG. 5 is an exemplary block diagram showing the use of the system of the present invention to perform closed loop control of a body function. In block 352, the SCU 302 requests status from microsensor A (SEA). The SCU 302, in block 354, then determines whether the present command given to a microstimulator is satisfactory and, if necessary, determines a new command and transmits the new command to the microstimulator A (STA) in block 356. For example, if microsensor A (SEA) is reading a voltage corresponding to the degree of contraction resulting from stimulating a muscle, the SCU 302 could transmit a command to microstimulator A (STA) to adjust the sequence of drive pulses, e.g., in magnitude, duty cycle, etc., and accordingly change the voltage sensed by microsensor A (SEA). Accordingly, closed loop, i.e., feedback, control is accomplished. The characteristics of the feedback (position, integral, derivative (PID)) control are preferably program controlled by the SCU 302 according to the control program contained in program storage 310.

Figure 6:
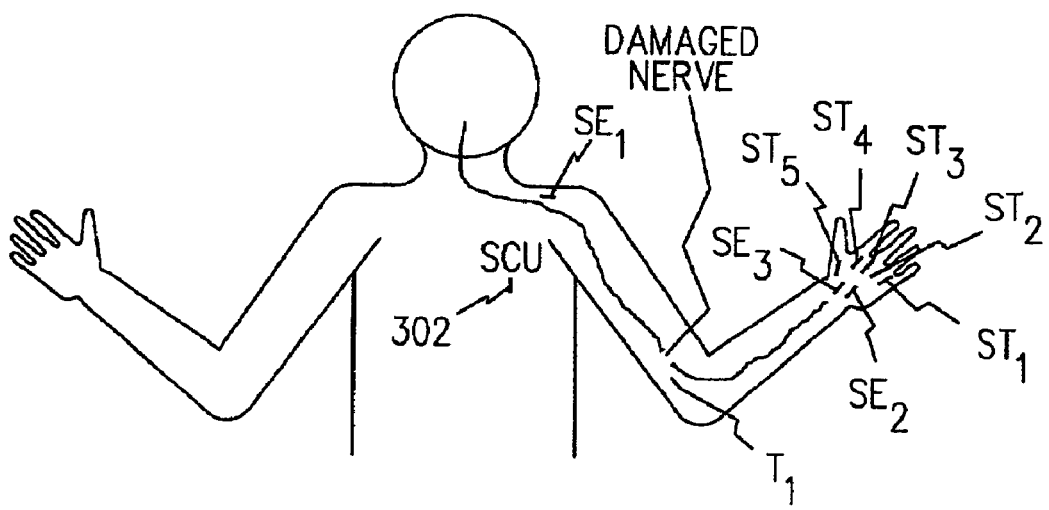
FIG. 6 shows an exemplary injury, i.e., a damaged nerve, and the placement of a plurality of implanted devices, i.e., microstimulators, microsensors and a microtransponder, under control of the system control unit for "replacing" the damaged nerve.

FIG. 6 shows an exemplary injury treatable by the present system 300. In this exemplary injury, the neural pathway has been damaged, e.g., severed, just above a patient's left elbow. The goal of this exemplary system is to bypass the damaged neural pathway to permit the patient to regain control of the left hand. An SCU 302 is implanted within the patient's torso to control a plurality of stimulators, ST1-ST5, implanted proximate to the muscles respectively controlling the patient's thumb and fingers (shown in the patient's hand for simplicity). Additionally, microsensor 1 (SE1) is implanted proximate to an undamaged nerve portion where it can sense a signal generated from the patient's brain when the patient wants hand closure. Optional microsensor 2 (SE2) is implanted in a portion of the patient's hand where it can sense a signal corresponding to stimulation/motion of the patient's pinky finger and microsensor 3 (SE3) is implanted and configured to measure a signal corresponding to grip pressure generated when the fingers of the patient's hand are closed. Additionally, an optional microtransponder (T1) is shown which can be used to improve the communication between the SCU 302 and the implanted devices.

Figure 7:
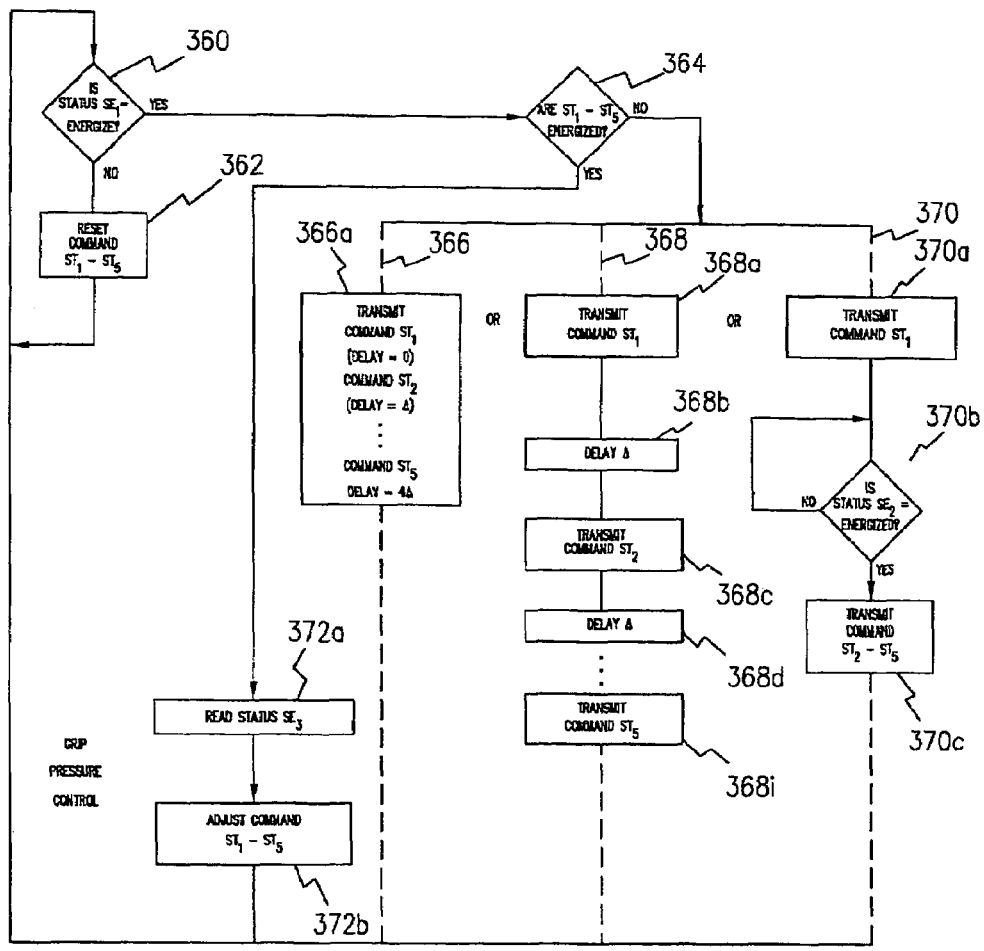
FIG. 7 shows a simplified flow chart of the control of the implanted devices of FIG. 6 by the system control unit.

FIG. 7 shows an exemplary flow chart for the operation of the SCU 302 in association with the implanted devices in the exemplary system of FIG. 6. In block 360, the SCU 302 interrogates microsensor 1 (SE1) to determine if the patient is requesting actuation of his fingers. If not, a command is transmitted in block 362 to all of the stimulators (ST1-ST5) to open the patient's hand, i.e., to de-energize the muscles which close the patient's fingers. If microsensor 1 (SE1) senses a signal to actuate the patient's fingers, the SCU 302 determines in block 364 whether the stimulators ST1-ST5 are currently energized, i.e., generating a sequence of drive/stimulation pulses. If not, the SCU 302 executes instructions to energize the stimulators. In a first optional path 366, each of the stimulators is simultaneously (subject to formatting and transmission delays) commanded to energize in block 366a. However, the command signal given to each one specifies a different start delay time. Accordingly, there is a stagger between the actuation/closing of each finger.

In a second optional path 368, the microstimulators are consecutively energized by a delay Δ. Thus, microstimulator 1 (ST1) is energized in block 368a, a delay is executed within the SCU 302 in block 368b, and so on for all of the microstimulators. Accordingly, paths 366 and 368 perform essentially the same function. However, in path 366 the interdevice timing is performed by the clocks within each implanted device 100 while in path 368, the SCU 302 is responsible for providing the interdevice timing.

In path 370, the SCU 302 actuates a first microstimulator (ST1) in block 370a and waits in block 370b for its corresponding muscle to be actuated, as determined by microsensor 2 (SE2), before actuating the remaining stimulators (ST2-ST5) in block 370c. This implementation could provide more coordinated movement in some situations.

Once the stimulators have been energized, as determined in block 364, closed loop grip pressure control is performed in blocks 372a and 372b by periodically reading the status of microsensor 3 (SE3) and adjusting the commands given to the stimulators (ST1-ST5) accordingly. Consequently, this exemplary system has enabled the patient to regain control of his hand including coordinated motion and grip pressure control of the patient's fingers.

Accordingly, to accomplish these tasks, such implantable devices must be able to interpret neurological signals from nerves and/or muscle tissues such that evoked muscular responses, neurologically sensed pressure or pain, e.g., touch, responses or the like may be detected and analyzed. The present invention is thus directed to an implementation of the sensor circuitry 188 for use in such an implantable device. Aspects of this invention are particularly directed to an implementation that is suitable for a small integrated circuit implementation that minimizes power, both of which features are particularly significant for use within the preferred microstimulator/microsensor environment.

Figure 8:
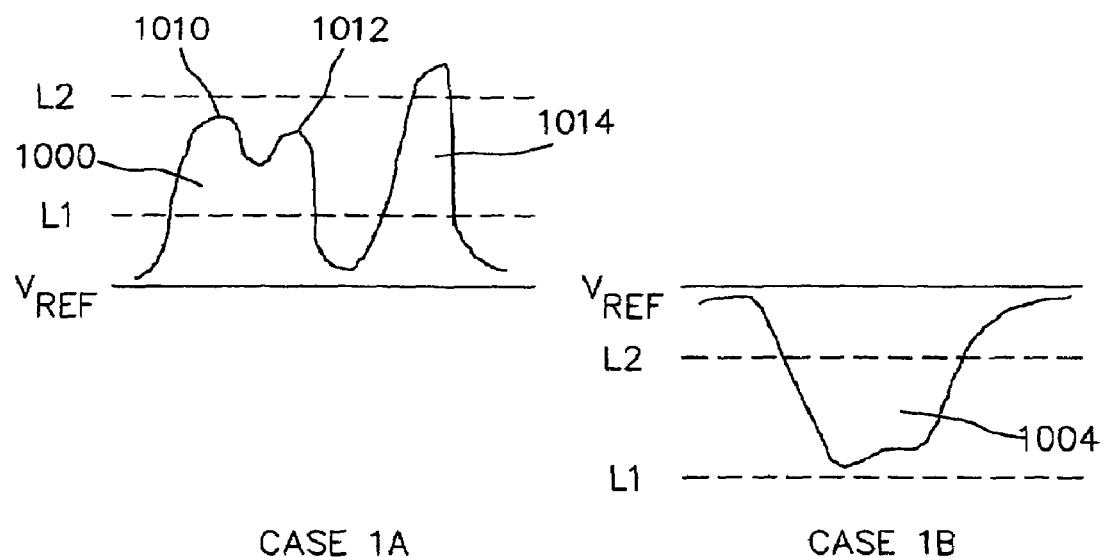
FIG. 8 shows exemplary monophasic neurological signals that may be analyzed by the signal analysis device of the present invention.
Figure 9:
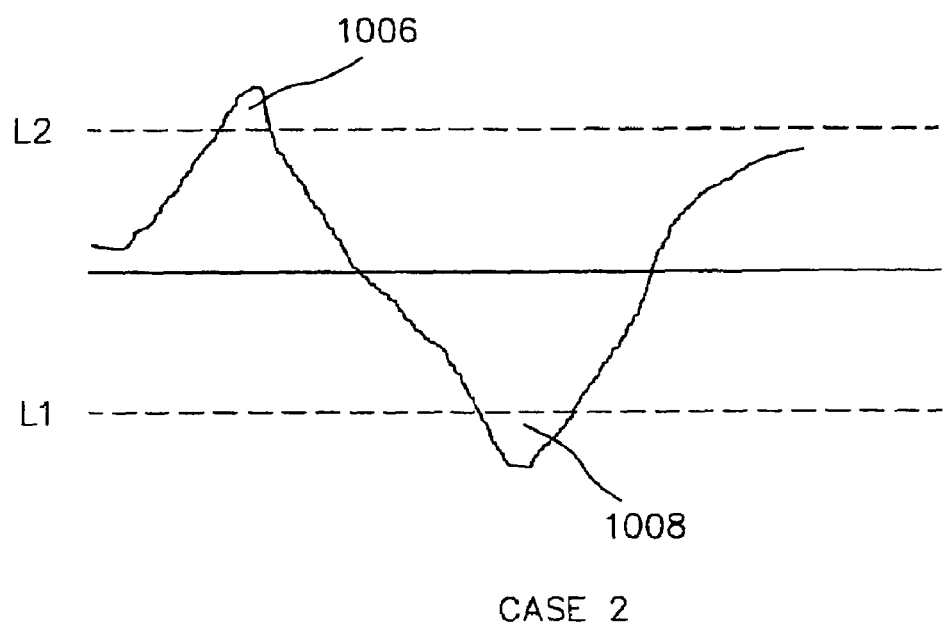
FIG. 9 shows an exemplary biphasic neurological signal that may be analyzed by the signal analysis device of the present invention.

Referring now to FIGS. 8 and 9, exemplary neurological waveforms are shown which have characteristics that are identifiable by embodiments of the present invention. For example, cases 1A and 1B of FIG. 8 respectively show events that are identified by monophasic positive or negative signal components; while case 2 of FIG. 9 shows an event that is identified by a positive, negative or positive and negative, i.e., biphasic, signal components.

Figure 10A:
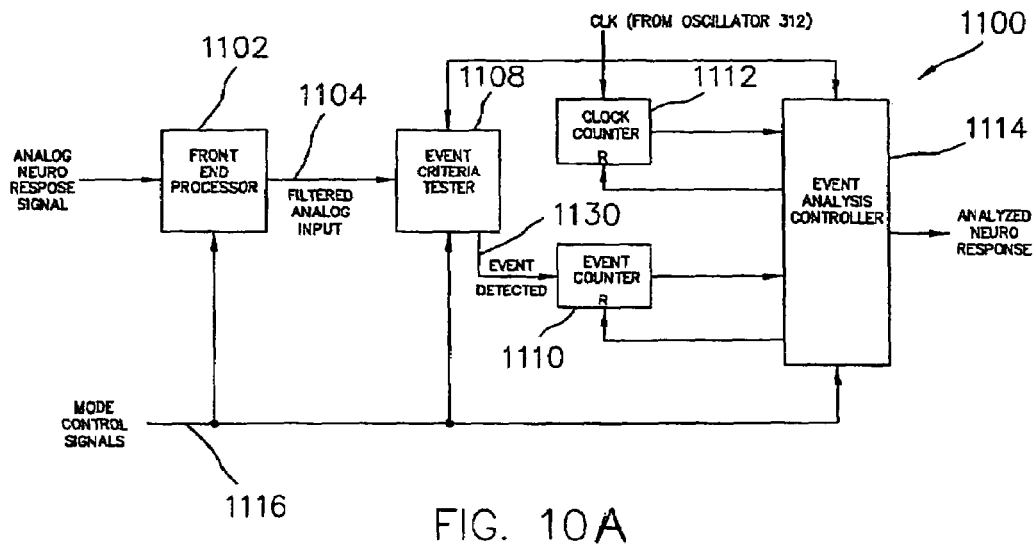
FIG. 10A shows a simplified block diagram of an exemplary signal analysis device of the present invention.

As an initial step, small analog voltages are sensed from the electrodes 112a, 112b and amplified and filtered at a front end processor 1102 of the sensor circuitry 188 (see FIG. 10). Next, this filtered analog input signal 1104 is processed according to various programmed criteria or modes.

In a first mode of operation (see FIG. 8), this filtered signal is alternatively compared with one or two (or more) programmed threshold levels, shown as L1 and L2. Voltage levels are shown with respect to a reference voltage Vref. These levels may be either positive or negative with respect to Vref. (It should be noted that the use of these threshold levels L1 and L2 is exemplary and the use of these threshold levels may be exchanged or substituted and the relationship of these threshold levels may be reversed as well. Furthermore, the use of only two threshold levels is exemplary and embodiments that identify events according to criteria including more than two thresholds is expressly recognized to be within the scope of the present invention.) In this first mode of operation, an event may be recognized by detecting an analog voltage signal extending above a first threshold level L1 (see signal portions 1000 and 1002 of case 1A) or extending below a second threshold level L2 (see signal portion 1004 of Case 1B).

Alternatively, in a second mode of operation, a second threshold level may be used to exclude signals from being detected as events. Thus, for detection in this mode, a signal must exceed a first threshold L1 without exceeding a second threshold L2. Thus, in case 1A, signal portion 1000 is identified as an event and signal portion 1002 is not. Case 1B shows an alternative of this mode where events are identified when the signal extends below a second threshold L2 without extending below a first threshold L1. Thus, in case 1B, signal portion 1004 is identified as an event.

In a next mode of operation (see FIG. 9), positive signal portions extending above a second threshold L2 or negative signal portions extending below a first threshold L1 are identified as events. Thus, case 2 shows two identifiable events corresponding to signal portions 1006 and 1008. In a variation of this next mode of operation, an identifiable event may be when a signal passes above a second threshold L2 and below a first threshold L1. Thus, in this variation, case 2 shows a single identifiable event.

Figure 11A:
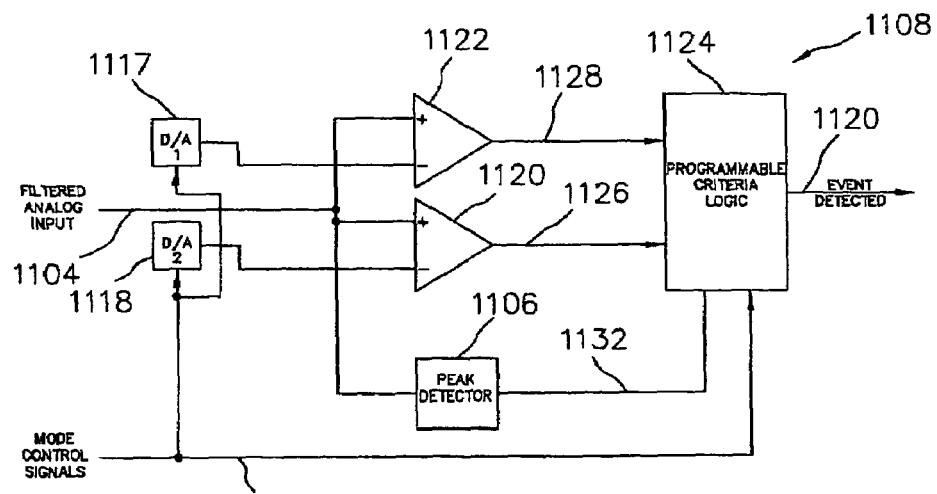
FIGS. 11A and 11B show preferred and alternative implementations of the event criteria tester of the exemplary embodiment of FIG. 10.
Figure 11B:
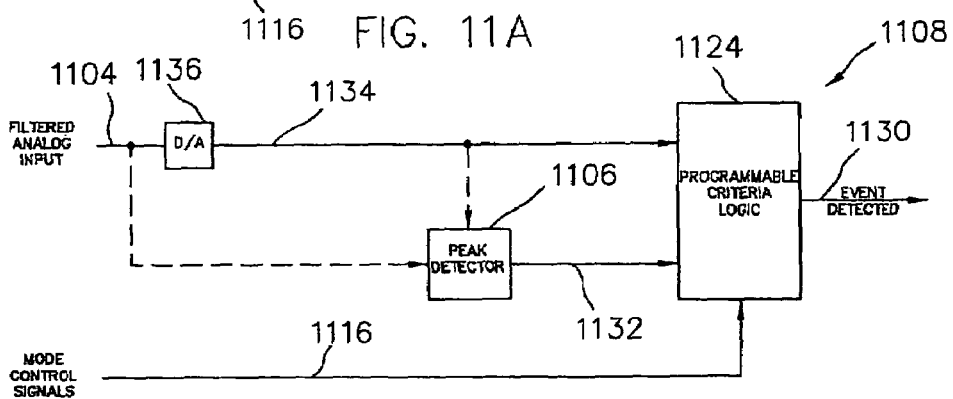

In a further mode of operation, peaks, i.e., zero slope portions, of the sensed signal are detected as events by a peak detector 1106 (see FIGS. 11A and 11B). Thus, in this mode, case 1A shows three identifiable events corresponding to signal peaks 1010, 1012 and 1014. In a variation of this mode of operation, only peaks between the two programmed threshold levels L1 and L2 are identified as events, i.e., peaks that occur above or below the threshold levels are excluded. Thus, in this mode variation, case 1A shows two identifiable events corresponding to peaks 1010 and 1012.

Finally, the peak detector 1106 (see FIGS. 11A and 11B) may be used to adapt the threshold levels to changes in the average peak values, e.g., by monitoring changes in the average peak values and adapting the threshold levels by the actual or percentage changes of the average peak values. Such a feature may be useful to compensate for tissue encapsulation of the electrodes or automatically adapting to different signal strengths that may be measured during implantation.

FIG. 10 shows a block diagram of an exemplary embodiment of the signal analysis device 1100 of the present invention. The signal analysis device 1100 comprises at least a portion of the aforementioned sensor circuitry 188. Signal analysis device 1100 is primarily comprised of: (1) sensing circuitry, i.e., front end processor 1102, for receiving a biological signal within the implantable device 100 and generating a sensed voltage output, i.e., filtered analog input signal 1104, in response thereto; (2) event detection circuitry, i.e., event criteria tester 1108, that is alternatively configurable to determine whether an event occurred according to one or according to two or more programmable criteria for detecting an attribute of the filtered analog input signal 1104 and designating the detected attribute as an event; (3) an event counter 1110 configured for accumulating detected events; (4) a clock counter 1112 accumulating clock pulses, preferably from clocks associated with oscillator 312; and (5) event analysis circuitry, i.e., event analysis controller 1114, configurable for operation in a plurality of modes of operation for determining a processed value corresponding to the detected events and the accumulated clock pulses.

Preferably, front end processor 1102 amplifies a neurological signal and bandpass filters the amplified signal according to programmable criteria transferred from controller circuitry 106 via mode control signal bus 1116. The resulting filtered analog input signal 1104 is provided to event criteria tester 1108 which detects identifiable signal components, i.e., events, as previously described in reference to FIGS. 8 and 9.

Figure 10B:
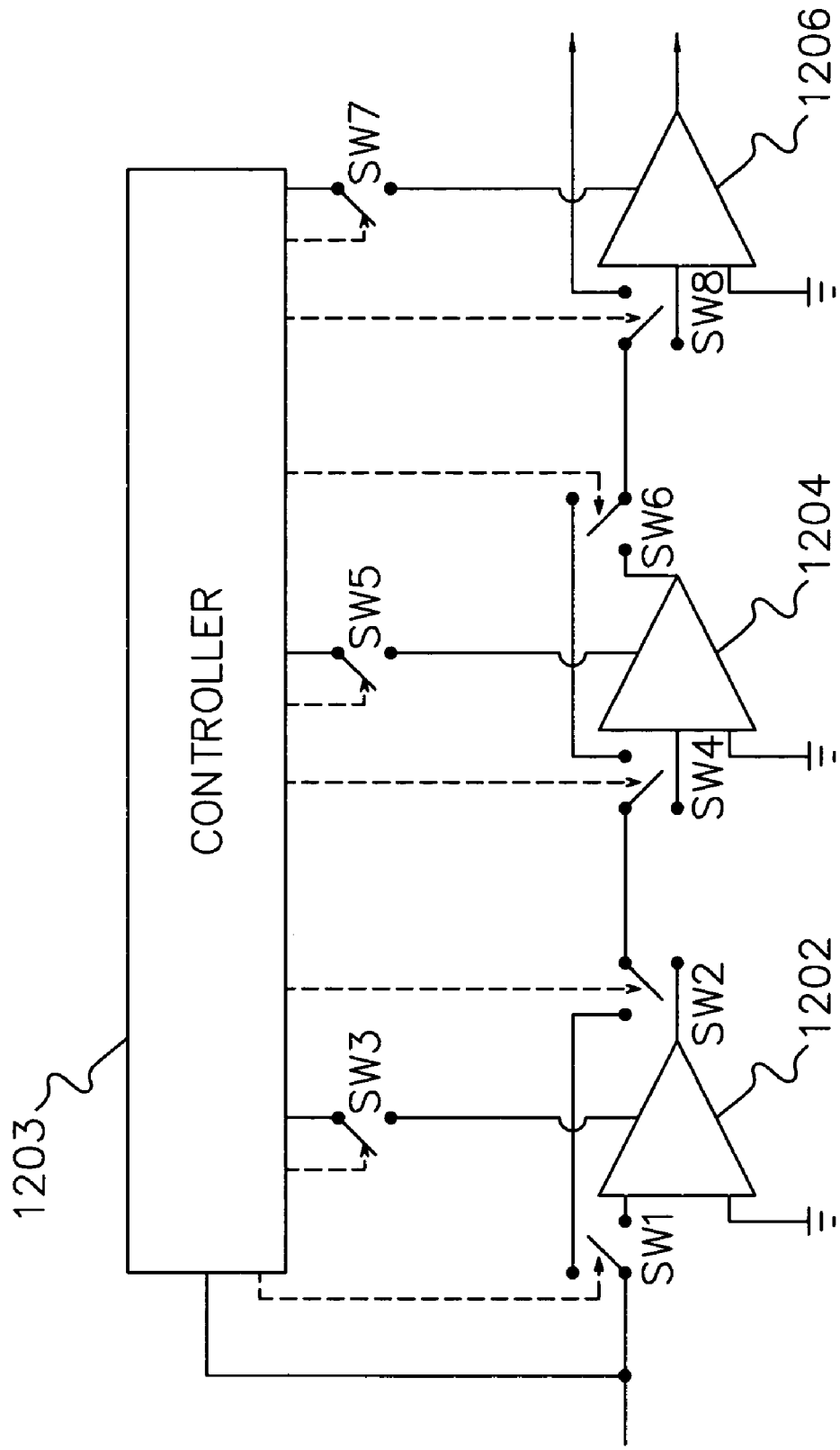
FIG. 10B is an illustration of an aspect of the front end processor 1102 comprising the amplifiers(s) as a portion of the sensor circuitry 188.

In the present embodiments, it is contemplated that the amplification of the biological/neurological signals (which are generally in the form of sensed electrical signals) is performed by utilizing a single amplifier or a set of cascaded amplifiers. It is contemplated that the amplifiers may be variable-gain low-noise amplifiers, thereby allowing for a change in the gain of the amplifiers by controlling the supply current to the respective amplifiers. FIG. 10B is an illustration of an aspect of the front end processor 1102 comprising the amplifier(s) as a portion of the sensor circuitry 188. Referring to FIG. 10B, a first switch SW1 is provided in order to couple the sensed electrical signals to a first amplifier 1202. The sensed electrical signals are also provided to a controller 1203 wherein the controller has the capability to measure and determine the magnitude of sensed electrical signals. In the event that the magnitude of sensed electrical signals is above a predetermined or desired threshold level, then the controller 1203 toggles the first switch SW1 to a bypass position such that the sensed electrical signals are not provided to the input of the first amplifier 1202 and instead bypass the first amplifier 1202 by utilizing the first switch SW1 and second switch SW2. In addition, the controller 1203 may open the third switch SW3 and cut off the supply current to the first amplifier 1202. As shown in FIG. 10B, a fourth switch SW4, a fifth switch SW5, and a sixth switch SW6 similarly provide for the bypassing of a second amplifier 1204, whereas a seventh switch SW7 and an eighth switch SW8 similarly provide for the bypassing of the third amplifier 1206.

In the present aspect of the front end processor 1102, it is contemplated that when the sensed electrical signals have a magnitude (such as voltage amplitude) above the predetermined or desired threshold level, then all of the amplifiers may be bypassed using the switches as described above. Moreover, in an alternate aspect, it is contemplated that the supply currents to the variable gain low-noise amplifiers may be increased or reduced responsive to the magnitude of the sensed electrical signals by the controller 1203, thereby affecting the amplification of the sensed electrical signals at the output of the amplifier(s).

In the present aspect, when the magnitude of the sensed signals is below the predetermined or desired threshold level, by coupling them to the input of any or all of the amplifiers the sensed electrical signals are amplified and provided to the next stage in the sensor circuitry 188.

It must be noted that in the present aspect of the front end processor 1102 by virtue of measuring and determining the magnitude of the sensed electrical signals by the controller 1203 and accordingly bypassing the relevant amplifier(s) or reducing the amount of current supplied to the respective amplifier(s) the power consumption in the implantable device is reduced and the battery life is extended.

FIGS. 11A and 11B describe a preferred and an alternate implementation of the event criteria tester 1108 of the present invention. In the preferred implementation of FIG. 11A, the event criteria tester 1108 is primarily comprised of (1) two or more digital to analog, i.e., D/A converters 1117 and 1118; (2) two or more analog comparators 1120 and 1122 and (3) programmable criteria logic 1124. In operation, the D/A converters 1117, 1118 receive programmable digital threshold values from the controller circuitry 106 via mode control signal bus 1116 that are latched internally. The D/A converters 1117, 1118 generate analog threshold values that are input to analog comparators 1120, 1122. Additionally, the comparators 1120, 1122 receive filtered analog input signal 1104 and generate signals 1126 and 1128 when the filtered analog input signal 1104 exceeds programmed threshold levels L1 and L2, respectively. Preferably, signals 1126 and 1128 are processed subject to hysteresis. Programmable criteria logic 1124 then processes signals 1126, 1128 and determines events according to programmable criteria (as previously discussed) received by the criteria logic 1124 from control circuitry 106 via mode control signal bus 1116. The programmable criteria logic generates an event detected signal 1130 according to the programmed criteria. This particular implementation provides the additional benefit that it minimizes power consumption. It is well known that for some "low power" digital logic, e.g., CMOS, the power consumption is a function of the number of logic transitions per unit time, e.g., frequency. By minimizing the number of digital logic transitions, the power consumption is accordingly minimized. D/A converters 1117, 1118 only experience digital logic transitions when they are initially loaded by the controller circuitry 106. Accordingly, the associated power consumption is extremely low. The programmable criteria logic 1124 only experiences transitions when the filtered analog signal crosses the programmed threshold levels, i.e., when there are transitions of signals 1126, 1128. These transitions occur at a fairly low rate and thus the associated power dissipation is also extremely low.

The implementation of FIG. 11A may additionally comprise a peak detector 1106 that receives an analog input from the filtered analog input signal 1104 and provides an output 1132 corresponding to detected peaks, i.e., points where the voltage slopes are zero, to the programmable criteria logic 1124. As previously described, whether or not the detected peaks correspond to events may be qualified or excluded according to where the peaks occur in relation to the programmed thresholds.

FIG. 11B shows an alternative implementation of the event criteria tester 1108 of FIG. 10 that primarily operates in the digital domain. According to this implementation, the filtered analog input signal 1104 is converted to a digital signal 1134 by analog to digital converter (A/D) 1136. This digital signal 1134 is then processed purely in the digital domain by the programmable criteria logic 1124. In this implementation, the mode control signal bus 1116 provides digital threshold values to the programmable criteria logic. Preferably, the programmable criteria logic 1124 performs its threshold comparisons using hysteresis as discussed in reference to FIG. 11A.

The implementation of FIG. 11B may additionally comprise a peak detector 1106 as described in relation to FIG. 11A. Alternatively, the peak detector 1106 may operate on the digital signal 1134. In a further alternative, the function of the peak detector 1106 may be incorporated into digital logic within the programmable criteria logic 1124.

The implementation of FIG. 11B offers the advantage that since it may be totally implemented as digital logic, it can conveniently take advantage of transistor size reductions as semiconductor processes improve (along with associated power reductions).

Finally, FIG. 12 shows an alternative "fully" digital embodiment of the present invention. In this embodiment, an optional A/D converter 1136 provides digital signal 1134 to a digital signal processor (DSP) 1138 where the aforedescribed functions are executed under software control. Advantageously in this embodiment, many DSPs include analog to digital converters and thus all or most of the functionality of the signal analysis device 1100 may be included within the. DSP, optionally including the front end filtering of the front end processor 1102 (in which case the front end processor 1102 may solely consist of an amplifier).

Figure 12A:
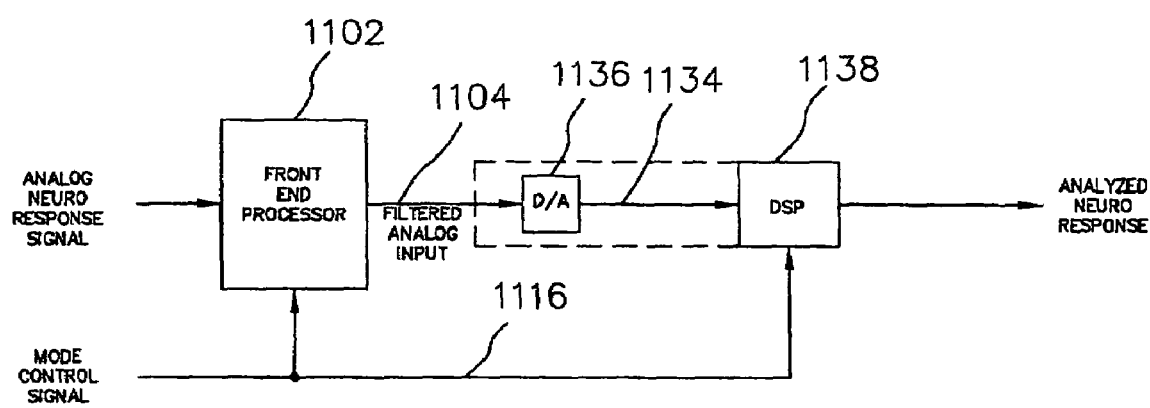
FIG. 12A shows an alternative "fully" digital implementation of the exemplary embodiment of FIG. 10.
Figure 12B:
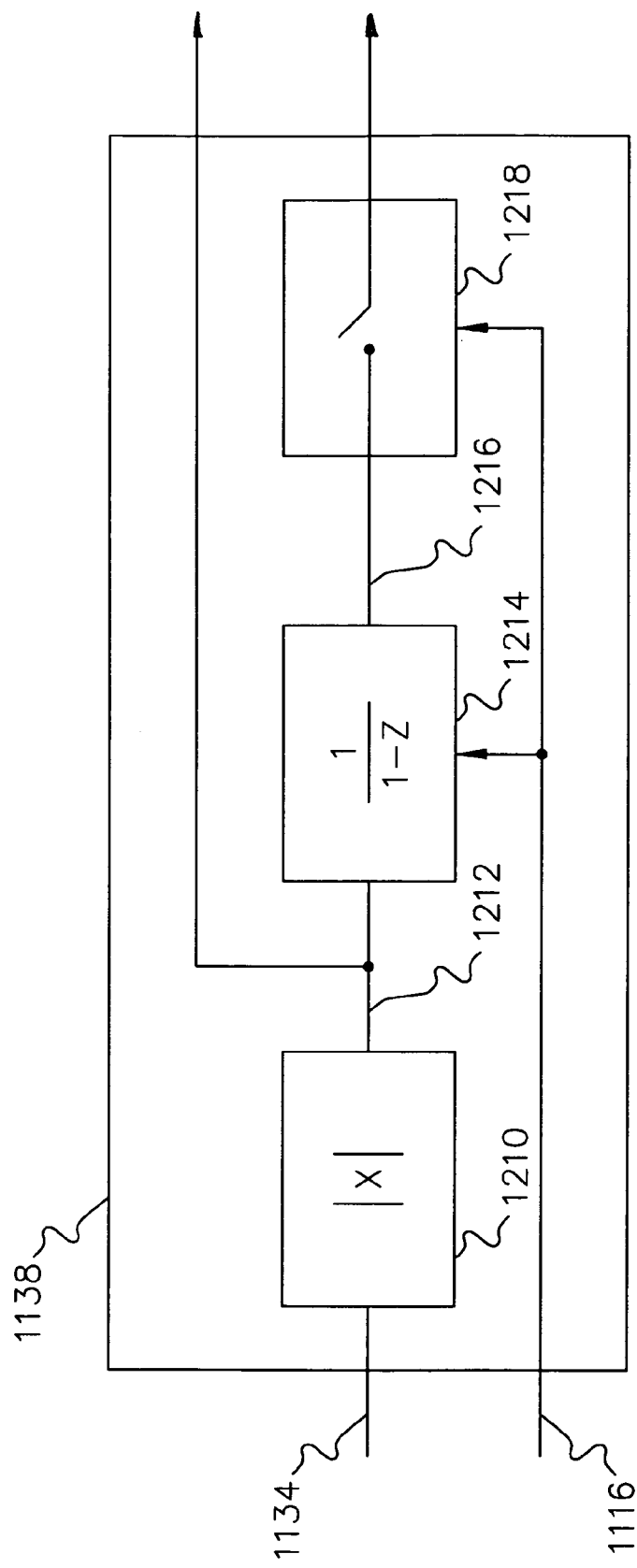
FIG. 12B is a more detailed illustration of the DSP shown in FIG. 12A.
Figure 13A:
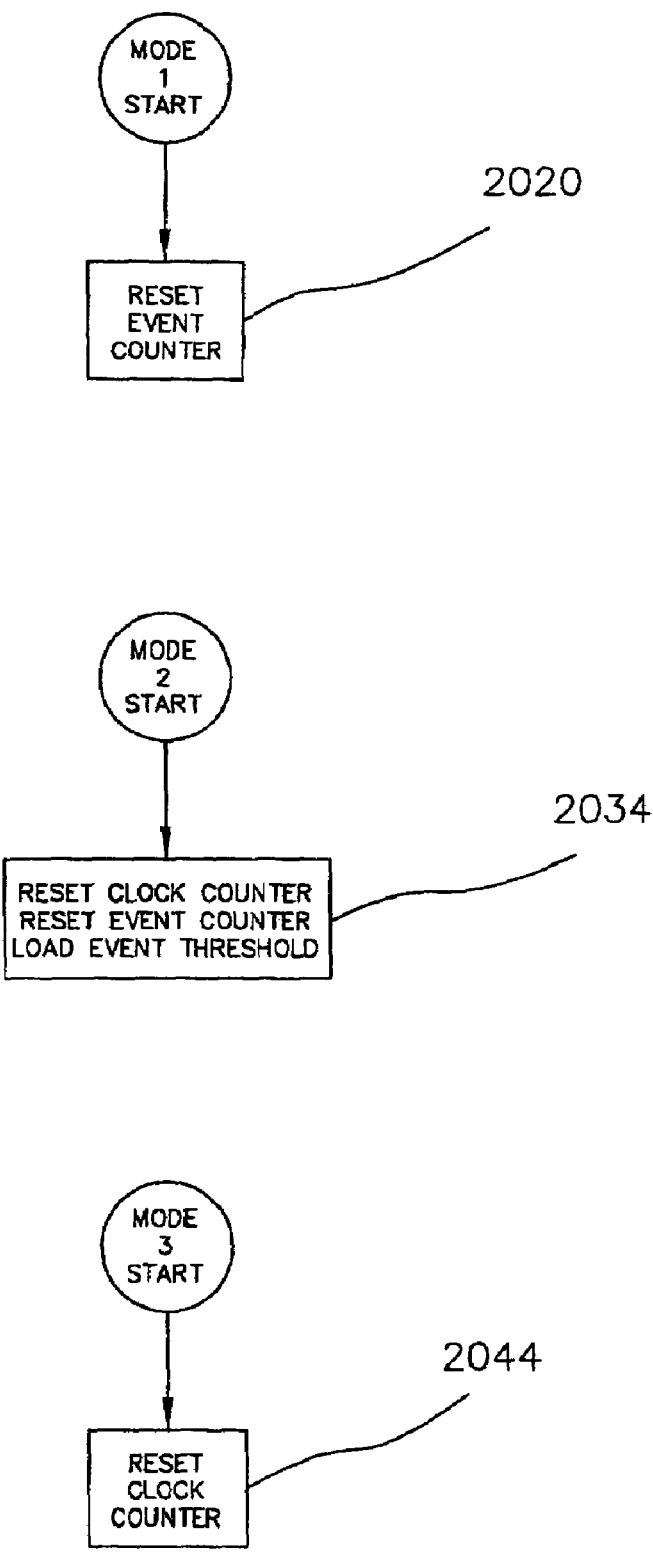
FIGS. 13A-D is an illustration of an exemplary flow chart for the operation of the signal analysis device of the present invention.
Figure 13B:
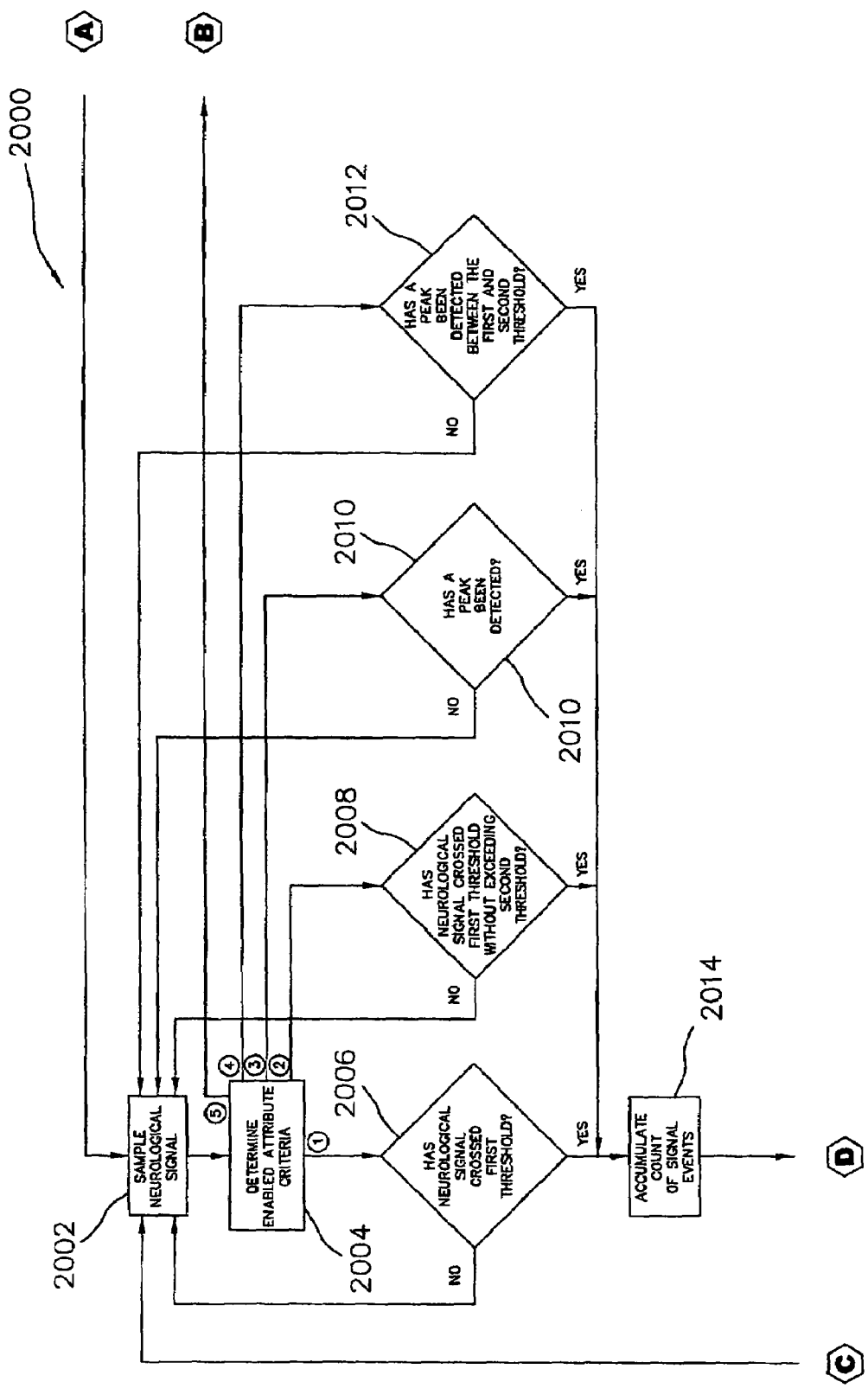
Figure 13C:
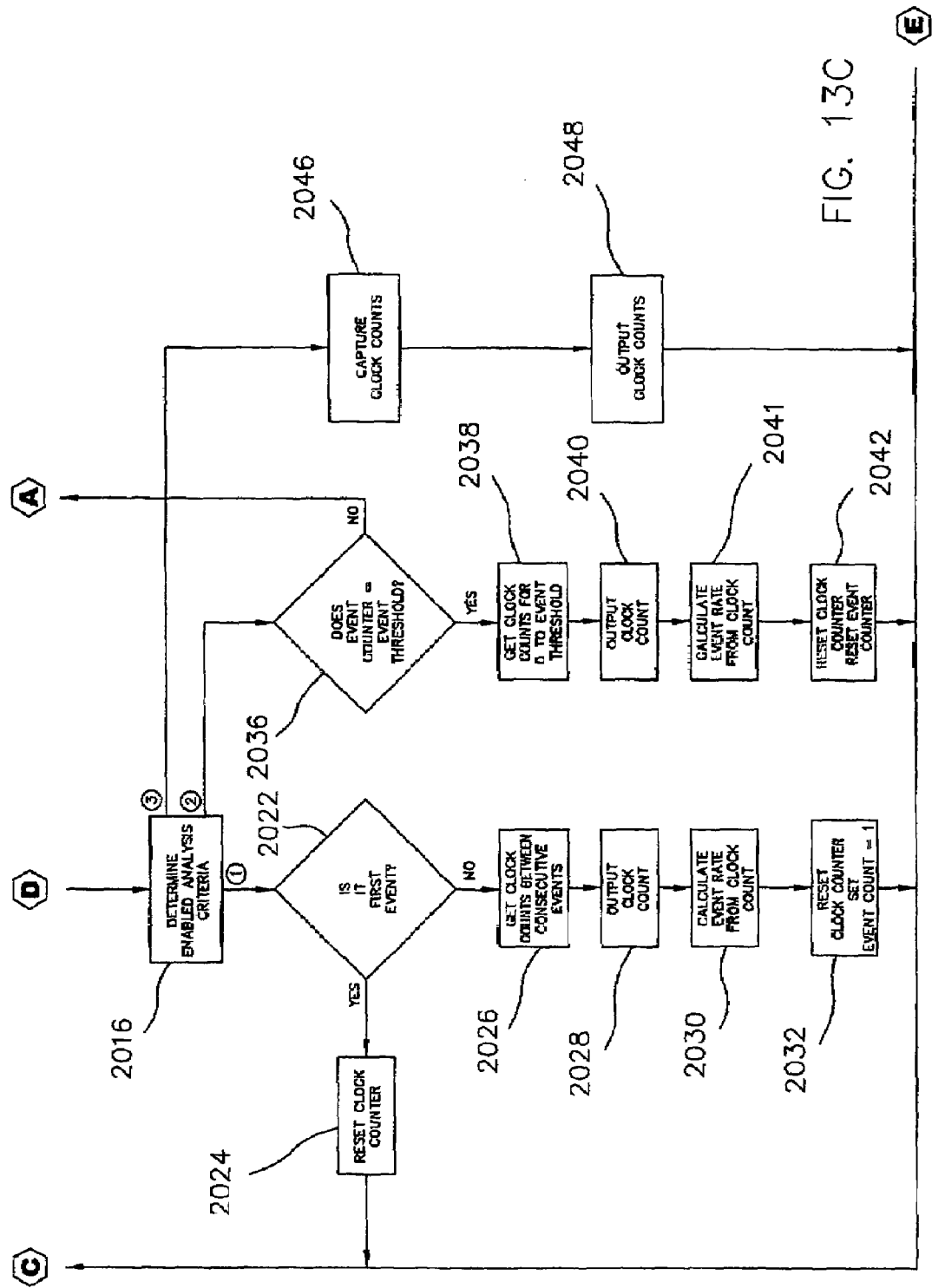
Figure 13D:
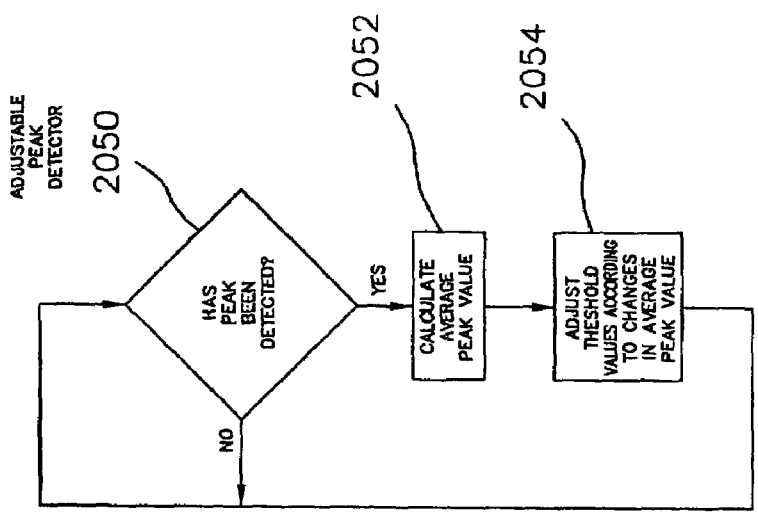
Figure 13D:
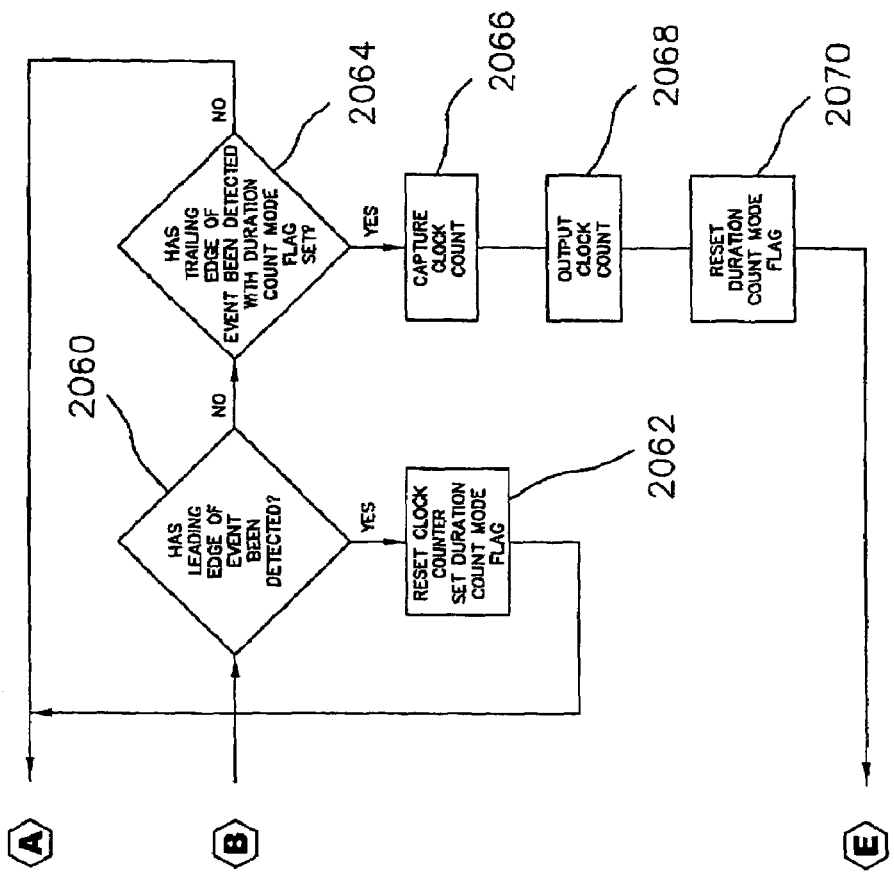

FIG. 12B is a more detailed illustration of the DSP shown in FIG. 12A. As shown in FIG. 12B, the DSP 1138 comprises a rectifier unit 1210 wherein it receives the digital signal 1134 and generates a rectified signal 1212. The rectified signal 1212 may be provided as an output of the DSP or in the alternative, the rectified signal may be provided to an integrator unit 1214 which in turn generates an integrated signal 1216 to be operated on by the decimator 1218 at a desired sample rate. The output of the DSP is an analyzed neuro-response signal that contains indicia of biopotential parameters of the tissue adjacent to the implantable device. Furthermore, it is contemplated that the output of the DSP 1138, which is substantially in the form of rectified and integrated sensed electrical signals, is provided to the transmitter for wireless transmission to receiving circuitry for further processing. Optionally, the integrated sensed electrical signals can be further averaged (not shown) utilizing circuitry and techniques known to those skilled in the art. It is contemplated that the integrated sensed electrical signals are averaged over a predefined range between about 1 nanosecond and about 3600 seconds, wherein the preferred averaging interval is about 10 milliseconds.

FIGS. 13A-D show an exemplary flow chart 2000 of the operation of the programmable signal analysis device 1100 of the present invention. Flow chart 2000 is directly applicable to the DSP implementation of FIG. 12 but one of ordinary skill in the art should appreciate that it is equally applicable to hardware or hardware/software implementations as shown in FIG. 10, FIG. 11A, and FIG. 11B.

In block 2002, the neurological signal received from electrodes 112a, 112b are amplified and filtered by front end processor 1102. According to the programmed attribute criteria, event criteria tester 1108 determines in block 2004 which criteria are enabled. In a first mode, block 2006 identifies events by determining whether the neurological signal has crossed a first threshold, e.g., L1. Alternatively in a second mode, block 2008 identifies events by determining whether the neurological signal has crossed a first threshold, e.g., L1, without crossing a second threshold, e.g., L2. In a variation of block 2008 (not shown), this mode may be accomplished by excluding mode 1 type events if the neurological signal has exceeded the second threshold. Alternatively, in a third mode, block 2010 identifies events by determining whether a peak has been detected. Alternatively, in a fourth mode, block 2012 identifies events by determining whether a peak has been detected between the first and second thresholds. In a variation of block 2012 (not shown), this mode may be accomplished by excluding mode 3 type events that do not occur between the two thresholds.

Once an event has been detected, block 2014 accumulates a count of signal events, e.g., in event counter 1110. Event analysis controller 1114 then analyzes, in block 2016, the accumulated events according to its programmed mode. In this example, three different exemplary modes are shown, mode 1 which determines an event rate (or clock count per event) by counting the clocks between events, mode 2 which counts a prescribed number of events and determines the rate by accumulating the clock counts for the prescribed number of events, and mode 3 which determines the number of clocks between a designated start time, e.g., corresponding to a stimulation pulse, and an event, e.g., an evoked response. Mode 3 is of particular use in analyzing cardiac responses.

When mode 1 is started, the event counter 1110 is reset in block 2020 and when the first event is detected in block 2022, the clock counter 1112 is reset in block 2024. Accordingly, when the next event is detected, a clock count between consecutive events is captured in block 2026. This clock count may be output in block 2028 or it may be processed along with the clock rate to determine an event rate in block 2030, e.g., a heart rate in beats per minute. Finally, in block 2032, the clock counter 1112 is reset and the event counter 1110 is set to not be the first event, e.g., set to a value of 1. Accordingly, this process may redetermine the event rate as of the occurrence of the next event by using the last detected event as the "first" event.

When mode 2 is started, the event counter 1110 and the clock counter 1112 are reset in block 2034. Additionally, an event threshold is loaded, i.e., the number of events that are to be counted before a result is reported. In block 2036, event counts are ignored until the event threshold is reached. Then, in block 2038, the clock counts are captured for the event threshold and this clock count value is optionally output in block 2040. Alternatively or additionally, the captured clock count and event threshold values are used to calculate an event rate in block 2041. Finally, in block 2042, the clock counter 1112 and the event counter 1110 are reset. Accordingly, this process may redetermine the event rate when the event counter 1110 re-accumulates an event count equal to the event threshold.

When mode 3 is started, the clock counter 1112 is reset in block 2044. This would typically correspond to the time that a stimulation pulse is emitted from the implantable device to stimulate muscle, e.g., cardiac, tissue. Preferably, in such a mode, there is a blanking period (not shown), in which the detection of events is suppressed, e.g., by blanking the response of the front end processor 1102 and/or suppressing accumulation or detection of events. Following this optional blanking period, the clock count is captured as of the first event, e.g., an evoked response, in block 2046 and the captured clock count value is output in block 2048.

As previously discussed, the peak detector may alternatively or additionally be used to adjust the threshold levels, e.g., L1 and L2. A background task to accomplish this feature is shown in blocks 2050-2054. In block 2050, it is determined whether a peak, a zero slope of the input signal, has been detected. If a peak has been detected, its voltage value is averaged with the prior peak values, e.g., with an analog or digital low pass filter, to achieve an average peak value. In block 2054, the trend or change in the average peak value is analyzed and the programmed threshold values are adjusted accordingly.

In a next alternative mode, the duration of an event is detected, e.g., the amount of time that a neurological signal is greater than a first threshold, e.g., L1, without exceeding a second threshold, e.g., L2. A simplified example of this next alternative mode is described in relationship to blocks 2060-2070. Following block 2040, a fifth attribute criteria mode is used in block 2060. In block 2060, it is determined whether the sensed neurological signal exceeds a first threshold (preferably programmable to additionally determine that the neurological signal has not exceeded a second threshold). It the first threshold has been crossed, then, in block 2062, the clock counter is reset and a duration count mode flag is enabled. The process then continues at block 2002. The next time through in block 2060, the leading edge of the neurological signal will not be detected, e.g., because the duration count mode flag is set and that flag identifies that the neurological signal already exceeds the first threshold. The process continues with block 2064 which determines if the trailing edge of the neurological signal has been detected while the duration count mode flag is set. Once this trailing edge is detected, the clock count is captured in block 2066 and output in block 2068. The duration count mode flag is then reset in block 2070. While the blocks 2060-2070 have essentially shown this function as being primarily implemented as a portion of the event criteria tester 1108, it is recognized that portions of this function may alternatively or additionally be implemented as part of the event analysis controller 1114.

While the invention herein disclosed has been described by means of specific embodiments and applications thereof, numerous modifications and variations could be made thereto by those skilled in the art without departing from the scope of the invention set forth in the claims. It is therefore to be understood that within the scope of the claims, the invention may be practiced other than as specifically described herein.

What is claimed is:

1. An implantable device comprising a sensing unit; wherein the sensing unit is adapted to rectify and integrate sensed electrical signals emanating from tissue adjacent said sensing unit; wherein the sensing unit comprises at least one amplifier, said at least one amplifier being under the control of a supply current; and wherein the at least one amplifier has a gain adjustable as a function of the supply current, the supply current being a function of the magnitude of the sensed electrical signals.

2. The implantable device of claim 1, further comprising a controller for receiving the sensed electrical signal and measuring the magnitude of the sensed electrical signal, wherein the controller controls the supply current to the at least one amplifier.

3. The implantable device of claim 2, wherein the supply current to the at least one amplifier is controlled as a function of the magnitude of the sensed electrical signals.

4. The implantable device of claim 3, wherein the supply current to the at least one amplifier is reduced or cutoff when the magnitude of the sensed electrical signals is above a predetermined threshold level.

5. The implantable device of claim 3, wherein the supply current to the at least one amplifier is increased when the magnitude of the sensed electrical signals is below a predetermined threshold level.

6. The implantable device of claim 1, wherein the implantable device comprises an elongate housing have an axial dimension of less than 60 mm and a lateral dimension of less than 6 mm.

7. The implantable device of claim 1, further comprising a transmitter for wirelessly transmitting the integrated rectified sensed electrical signals to receiving circuitry for further processing.

8. The implantable device of claim 7, wherein the integrated sensed electrical signals are averaged over a predefined range between about 1 nanosecond and about 3600 seconds.

9. The implantable device of claim 8, wherein the integrated sensed electrical signals are averaged over an interval of about 10 milliseconds.

10. An implantable device, comprising:
    a sensing unit for sensing electrical signals, said sensing unit adapted to rectify and integrate said sensed electrical signals;
    a controller for receiving said sensed electrical signals;
    at least one amplifier for receiving the sensed electrical signals, wherein the at least one amplifier receives supply current from the controller and wherein the supply current to the at least one amplifier is based on the magnitude of the sensed electrical signals.

11. The implantable device of claim 10, wherein the controller measures the magnitude of the sensed electrical signals and wherein the supply current to the at least one amplifier is reduced or cutoff when the magnitude of the sensed electrical signals is above a predetermined threshold level.

12. The implantable device of claim 10, wherein the controller measures the magnitude of the sensed electrical signals and wherein the supply current to the at least one amplifier is increased when the magnitude of the sensed electrical signals is below a predetermined threshold level.

13. An amplification system adapted for use in an implantable medical device, said system having a system gain, a system input and a system output, the system comprising:
    a plurality of amplifiers in switchable series circuit arrangement, between the system input and the system output, each amplifier having a corresponding adjustable gain; and
    a controller coupled to each one of the plurality of amplifiers, said controller adapted to switch one or more of the amplifiers into series circuit arrangement, between the system input and the system output, as a function of a sensed parameter, such that the system gain is the product of the corresponding amplifier gain of the amplifiers switched into series circuit arrangement.

14. The amplification system of claim 13, wherein the controller is adapted to adjust the gain of each one of the plurality of amplifiers as a function of the sensed parameter.

15. The amplification system of claim 14, wherein each amplifier operates under the control of a supply current and wherein the controller is adapted to adjust the gain of an amplifier as a function of the sensed parameter, by adjusting the supply current to the respective amplifier.

16. The amplification system of claim 15, wherein the sensed parameter has a measurable value and wherein the controller configures the amplification system to include one or more amplifiers in series circuit arrangement between the system input and system output when the sensed parameter value is below a predetermined threshold value.

17. The amplification system of claim 16, wherein the number of amplifiers configured by the controller to be in series circuit arrangement is a function of the measured sensed parameter value.

18. The amplification system of claim 17, wherein the controller is adapted to remove the supply current from amplifiers not included in the series circuit arrangement.

19. The amplification system of claim 17, wherein the controller is adapted to remove all the amplifiers from the series circuit arrangement and couple the system output to the system input when the sensed parameter value is above a predetermined value.

20. The amplification system of claim 19, wherein the controller is adapted to remove the supply current from all the amplifiers not included in the series circuit arrangement.

* * * * *